(12) United States Patent
Kelly et al.

(10) Patent No.: US 11,682,475 B2
(45) Date of Patent: Jun. 20, 2023

(54) MAXIMIZING PATIENT REFERRAL OUTCOME THROUGH HEALTHCARE UTILIZATION AND/OR REFERRAL EVALUATION

(71) Applicant: EMBLEMHEALTH, INC., New York, NY (US)

(72) Inventors: Timothy Kelly, New York, NY (US); Zoe Yang, Brooklyn, NY (US)

(73) Assignee: EMBLEMHEALTH, INC., New York, NY (US)

( * ) Notice: Subject to any disclaimer, the term of this patent is extended or adjusted under 35 U.S.C. 154(b) by 382 days.

(21) Appl. No.: 16/801,710

(22) Filed: Feb. 26, 2020

(65) Prior Publication Data
US 2021/0265030 A1   Aug. 26, 2021

(51) Int. Cl.
*G16H 15/00* (2018.01)
*G16H 40/20* (2018.01)
(Continued)

(52) U.S. Cl.
CPC ............. *G16H 15/00* (2018.01); *G16H 10/60* (2018.01); *G16H 40/20* (2018.01); *G16H 80/00* (2018.01)

(58) Field of Classification Search
CPC ........ G16H 10/00; G16H 15/00; G16H 10/60; G16H 40/20; G16H 80/00
See application file for complete search history.

(56) References Cited

U.S. PATENT DOCUMENTS 6,014,629 A   1/2000   Debruin-ashton
7,558,738 B1  7/2009   Flatt
(Continued)

FOREIGN PATENT DOCUMENTS

CN   102103654 A   6/2011
CN   102609619 A   7/2012
(Continued)

OTHER PUBLICATIONS

Oderkirk, Readiness of electronic health record systems to contribute to national health information and research, Nov. 30, 2017, OECD Health Working Papers, No. 99, pp. 1-78. (Year: 2017).*
(Continued)

*Primary Examiner* — Christopher L Gilligan
(74) *Attorney, Agent, or Firm* — Peter Jensen-Haxel

(57) ABSTRACT

Disclosed is a method, a device, a system and/or a manufacture of maximizing patient referral outcome through healthcare utilization and/or referral record evaluation. In one embodiment, a method includes generating a healthcare utilization log and/or referral log with a determined (POS) value and/or a type of service value. A referral request is generated, including a referral profile of a patient. A reduced dataset matching the referral profile is generated from a utilization dataset and/or a referral dataset. The method then calculates a POS utilization rate, an inbound re-referral rate, and/or additional values of a healthcare provider represented in the reduced dataset. A utilization ruleset and/or a referral ruleset is applied to score and/or rank the healthcare provider. A referral data including a UID of the healthcare provider is transmitted over a network from a server to a computing device running a point-of-care application. The referral is selected and automatically scheduled.

20 Claims, 18 Drawing Sheets

(51) Int. Cl.
    *G16H 80/00*     (2018.01)
    *G16H 10/60*     (2018.01)

(56) References Cited

U.S. PATENT DOCUMENTS

| | | | |
|---|---|---|---|
| 7,904,315 B2 | 3/2011 | Sullivan | |
| 8,126,738 B2 | 2/2012 | Green | |
| 8,185,407 B2 | 5/2012 | Brimdyr | |
| 8,660,857 B2 | 2/2014 | Ebadollahi | |
| 9,996,666 B1 * | 6/2018 | Wilson | G06F 16/9537 |
| 2006/0143997 A1 | 7/2006 | Libenson | |
| 2013/0304485 A1 | 11/2013 | Khan | |
| 2014/0278462 A1 | 9/2014 | Jones | |
| 2015/0073824 A1 | 3/2015 | Norris | |
| 2015/0221046 A1 | 8/2015 | Roy | |
| 2015/0356248 A1 | 12/2015 | Kogan | |
| 2016/0071171 A1 | 3/2016 | Canceliere, III | |
| 2017/0103177 A1 * | 4/2017 | Iliff | G06Q 10/06393 |
| 2017/0270253 A1 | 9/2017 | Haider | |
| 2019/0005587 A1 | 1/2019 | Sharifi Sedeh | |
| 2019/0237203 A1 | 8/2019 | Schwabl | |
| 2019/0244700 A1 | 8/2019 | Aganyan | |
| 2019/0333613 A1 * | 10/2019 | Zaidi | G16H 40/63 |
| 2021/0043310 A1 * | 2/2021 | Valuck | G06Q 30/018 |
| 2021/0043320 A1 * | 2/2021 | Malkenson | G16H 10/60 |
| 2021/0134444 A1 * | 5/2021 | Redlus | G16H 50/30 |

FOREIGN PATENT DOCUMENTS

| | | | | |
|---|---|---|---|---|
| CN | 108305674 A | | 7/2018 | |
| CN | 109841273 A | | 6/2019 | |
| CN | 110010214 A | * | 7/2019 | |
| CN | 110010240 A | | 7/2019 | |
| TW | I647653 B | | 9/2017 | |
| WO | WO-2005093613 A1 | * | 10/2005 | G06Q 10/10 |
| WO | WO2015154058 A1 | | 8/2015 | |
| WO | WO2016061864 A1 | | 4/2016 | |

OTHER PUBLICATIONS

Chih-Lin Chi et. al., "Building a hospital referral expert system with a Prediction and Optimization-Based Decision Support System algorithm", Journal of Biomedical Informatics, vol. 41, Issue 2, pp. 371-386, published in May 2008.

* cited by examiner

FIG. 6  UTILIZATION LOG GENERATION PROCESS FLOW 650

FIG. 7  REFERRAL PROFILE GENERATION PROCESS FLOW 750

FIG. 8    REFERRAL EVALUATION PROCESS FLOW 850

REFERRAL SELECTION
PROCESS FLOW 950

LOG DATA STRUCTURE
1050

REFERRAL LOG
PROCESS FLOW 1150

*FIG. 12*  UTILIZATION LOG ASSOCIATION PROCESS FLOW 1250

*FIG. 13*  REFERRAL PROFILE GENERATION PROCESS FLOW 1350

REFERRAL EVALUATION PROCESS FLOW 1450

PATIENT SELECTION
PROCESS FLOW 1550

LOG DATA STRUCTURE
1650

*FIG. 17*  COMPLEX PROVIDER EVALUATION PROCESS FLOW 1750

MAXIMIZING PATIENT REFERRAL OUTCOME THROUGH HEALTHCARE UTILIZATION AND/OR REFERRAL EVALUATION

FIELD OF TECHNOLOGY

This disclosure relates generally to data processing devices and, more particularly, to a method, a device, and/or a system of maximizing patient referral outcome through healthcare utilization and/or referral record evaluation.

BACKGROUND

It may be a fundamental interest of a healthcare provider and/or a healthcare network that a patient has a positive outcome in receiving healthcare services. An important factor in creating a positive outcome is ensuring patient accessibility (which may also be referred to as "access") to the healthcare services. For example, high degree and/or sufficient amount of access may mean that the patient has a healthcare provider nearby where the patient resides, that the patient is seen by the healthcare provider promptly, that any subsequent procedures are performed on time, and/or that special needs of the patient can be accommodated. What may be another important factor in a positive outcome is value of the healthcare services provided. Value may be based on a number of factors, but may for example be based on an appropriate balancing of monetary cost, healthcare service complexity (e.g., complexity of a procedure, recovery time, side effects), and/or risk access considerations.

The healthcare industry may be facing increasing pressure to provide positive patient outcomes, including increased access and value in providing healthcare services. For example, payers (such as employers, insurance companies, and government agencies such as the Center for Medicare and Medicaid Services) may be shifting some reimbursement practice to promote value-based competition.

What may be a major factor in generating positive patient outcomes is an efficient referral process of the patient between healthcare providers. A first healthcare provider, called the "referring provider," will generally refer a patient to a different healthcare provider, called a "referral provider," when the referring provider is not qualified or otherwise able to provide a needed healthcare service for the patient. Referrals within the healthcare industry are common, especially within a healthcare network (e.g., an HMO, an ACO). A healthcare provider may be an individual, such as a solo clinician licensed to practice medicine or provide medical services (who may be referred to as an "individual provider"). The healthcare provider may also be a hospital, group of individual health professionals, or other business entity or other organization, some or all of which are licensed to practice a health provision or to perform health care services (which may be referred to as a "group provider"). Healthcare providers also generally desire for referred patients to be transferred efficiently, with an emphasis on good access to medical services once the patient is transferred to the referral provider.

The referral process in which the patient is referred from one healthcare provider to another can pose challenges to maximizing patient outcome, including access to and/or value of healthcare services. First, the referring provider may generally have little or no ability to gather or assess information about a referral provider. For example, referrals may be made based on habit or subjective criteria such as general notoriety within a healthcare network rather than awareness of any information related to patient outcome. This may partially occur for practical reasons because the referring provider has little time (e.g., 20-minute appointments of a clinician) and/or any evaluation assessment of referral providers may be a discrete process from providing the healthcare service.

Even where referrals may be optimal at one time (e.g., in terms of value and/or access), they may later become sub-optimal. Access and/or value of a referral provider may change on a monthly, daily, or even real-time basis. For example, even a healthcare provider providing historically high-value healthcare services may be a poor referral provider at a given time because they have low access. Such a referral provider may have a patient backlog, diminished capacity due to retiring clinicians, or have changed facilities and/or locations.

Access and/or value may also be context dependent, for example varying based on the circumstances and/or needs of the patients. A healthcare provider with generally good access and value for orthopedic surgeries may not provide more specific surgery (e.g., hand surgery) with good access or at high value. Conversely, a healthcare provider may be known to provide excellent access and good value for a given procedure, but may not excel in a broader category of healthcare services or may not excel in other defined incentives that may shift behaviors toward increased value and/or access.

Finally, even where some data-based and/or objective insight may be present and available to a clinician at the time a referral must be made, it may be difficult for a healthcare provider and/or healthcare network to promote its values or policies related to access and/or value. For example, there may be a challenge in communicating insights to the healthcare providers of the network.

One or more of these challenges may result in detriment to one or more of the stakeholders of a healthcare network. Patients may not receive healthcare services promptly, may not receive healthcare services best suited for their particular needs, and/or may decide not to receive healthcare services where the value and/or access is low, raising their health risk and potentially long-term cost when a health issue is not efficiently addressed. Healthcare providers working hard to establish good access and high value may not be rewarded with referrals that would reinforce their positive efforts. Healthcare providers lose revenue and may be at increased risk of malpractice where patients are not met with sufficient access. Payers may pay increased amounts and may therefore continue to support sub-optimal referral and/or healthcare utilization practices. On what may be a larger scale, a healthcare network may continue to operate with inefficiencies, resulting in network-wide sub-optimal value and access that can affect patient loyalty, damage reputation and brand stature, increase long-term health care costs, and/or reduce long-term revenue. There is a continuing need for technologies that support and increase the efficiency of the referral process.

SUMMARY

Disclosed are a method, a device, and/or a system of maximizing patient referral outcomes through healthcare utilization and/or referral record evaluation.

In one embodiment, a method for optimal determination of a healthcare referral provider includes determining generation of a healthcare utilization record that includes a patient UID (unique identifier) of a first patient and a provider UID of a first healthcare provider. A place of service value associated with the healthcare utilization record is determined along with a type of service associated with the healthcare utilization record. A first utilization log is generated comprising the provider UID of the first healthcare provider, the place of service value, the type of service value, and optionally comprising a utilization time associated with providing a healthcare service to the patient and/or associated with generation of the healthcare utilization record.

The method initiates a referral request to refer a second patient of a second healthcare provider to a referral provider. A referral profile is generated for the second patient, the referral profile including a place of service range, a type of service range, and optionally a time range. The referral profile is compared to a utilization dataset comprising a set of utilization logs extracted from a utilization database including the first utilization log. A reduced dataset is generated that includes a subset of utilization logs extracted from the utilization dataset matching the referral profile.

The method calculates, using the subset of utilization logs in the reduced dataset, a POS utilization rate of the first healthcare provider for each instance of the place of service value within the place of service range. A utilization ruleset is then applied to score, rank, and/or qualify the first healthcare provider based on criteria comprising the POS utilization rate.

The provider UID of the first healthcare provider is added to a referral data. The referral data is transmitted over a network from a server to a computing device of the second healthcare provider running a point-of-care application. The referral data is integrated within a user interface of a clinical documentation workflow of the point-of-care application.

A patient profile of the first patient may be queried with the patient UID of the first patient. The method may also extract from the patient profile of the first patient a patient data that includes a demographic data of the first patient, a coverage type of the first patient, and/or a diagnosis code of the first patient. The first utilization log may further include the patient data, and the referral profile may further include a patient data range. The patient data range may include a demographic data of the second patient, a coverage type of the second patient, and/or a diagnosis code of the second patient.

The method may calculate, using a set of utilization logs of two or more healthcare providers within the utilization database, a POS utilization rate for each instance of the place of service value within the place of service range. The scoring, the ranking, and/or the qualifying of the first healthcare provider may be based on criteria that includes the POS utilization rate of the first healthcare provider relative to a statistical average of the POS utilization rate calculated from the utilization database.

The method may receive a selection of the second healthcare provider from a clinician through the point-of-care application. The method may also automatically schedule an appointment for the second patient with the first healthcare provider. The patient profile of the second patient may include a location data associated with the second patient. The second healthcare provider may be determined to be within a predetermined distance based on the location data.

The utilization ruleset may determine that an instance of the place of service value is a preferred instance of the place of service value based on criteria comprising the type of service. The type of service value may be a service category and/or a procedure code value. The procedure code value may be a CPT code value. The place of service value may be stored in computer memory as a POS code value. The place of service range, the type of service range, the patient data range, and/or the time range of the referral profile may be selected by the clinician through the point-of-care application.

In another embodiment, a method for maximizing healthcare referral outcomes includes detecting a first healthcare referral of a first patient, the first healthcare referral from a first healthcare provider to a second healthcare provider. A first referral log is generated that includes a provider UID of the first healthcare provider, a provider UID of the second healthcare provider, a referral time of the first healthcare referral, and a type of service. The first referral log is stored in a computer memory.

The method detects a second healthcare referral of the first patient. The second healthcare referral is made from the first healthcare provider to a third healthcare provider. The method generates a second referral log that includes the provider UID of the first healthcare provider, a provider UID of the third healthcare provider, a referral time of the second healthcare referral, and the type of service. The second referral log is stored.

The method determines a referral association between the first healthcare referral and the second healthcare referral and stores a first database association linking the second referral log and the first referral log, and a referral request is initiated to refer a second patient to a referral healthcare provider.

A referral profile for the second patient is generated, the referral profile including a type of service range and optionally a place of service range. The referral profile is compared to a referral dataset that includes a set of referral logs associated with the provider UID of the first healthcare provider. A reduced dataset is generated including a subset of referral logs extracted from the referral dataset matching the referral profile. The first referral log and/or the second referral log is determined to match the referral profile.

A first time period value is referenced. The method calculates, using the subset of referral logs in the reduced dataset, an inbound re-referral rate of the second healthcare provider within the first time period value. A referral ruleset is applied to score, rank, and/or qualify the second healthcare provider based on criteria comprising the inbound re-referral rate of the second healthcare provider. The provider UID of the second healthcare provider is added to a referral data.

In yet another embodiment, a system includes a log server and a referral server communicatively coupled over a network. The log server includes a processor of the log server, a memory of the log server, and a set of healthcare utilization logs. Each of the utilization logs includes the provider UID of a healthcare provider, one or more instances of a type of service value, and one or more instances of a place of service value. The log server also includes a set of healthcare referral logs, each including the provider UID of the healthcare provider as a referral provider, a provider UID of a referring provider, one or more instances of the type of service value, and one or more instances of the place of service value.

A first set of database associations associate one or more of the set of healthcare utilization logs with one or more of the set of healthcare referral logs, and a second set of database associations associate one or more of the set of healthcare referral logs with one or more of a different set of healthcare referral logs from the referring provider to a different healthcare provider as a different referral provider.

The referral server includes a referral request agent comprising computer readable instructions that when executed on the processor of the of the referral server receives a referral request to refer a patient for healthcare services and generates and/or receives a referral profile. The referral server also includes a profile matching engine including computer readable instructions that when executed on the processor of the of the referral server compares the referral profile to the set of healthcare referral logs and the set of healthcare utilization logs, and then determines matching instances of the set of healthcare utilization logs and the set of referral logs to the referral profile.

The referral server also includes a dataset reduction subroutine having computer readable instructions that when executed on the processor of the of the referral server generates a reduced dataset that includes a subset of the set of utilization logs and a subset of the set of referral logs matching the referral profile.

A utilization rate routine of the referral server includes computer readable instructions that when executed on the processor of the of the referral server calculates, using the subset of utilization logs in the reduced dataset, a POS utilization rate of a referral healthcare provider for each instance of the place of service value. A referral rate routine of the referral server includes computer readable instructions that when executed on the processor of the of the referral server calculates, using the subset of referral logs in the reduced dataset, an inbound re-referral rate of the referral healthcare provider.

The system also includes, stored within the referral server, a hybrid ruleset specifying criteria to score, rank, and/or qualify the healthcare provider based on criteria that includes the POS utilization rate and the inbound re-referral rate. A referral generation subroutine includes computer readable instructions that when executed on the processor of the of the referral server generates a referral data that includes the provider UID of the referral provider, a name of the referral provider, and optionally a referral evaluation data including a score, a rank, and/or a qualification resulting from application of the hybrid ruleset on the reduced dataset. The system may further include a record server and a computing device that may run a point of care application. Other features of the present embodiments will be apparent from the accompanying drawings and from the detailed description that follows.

BRIEF DESCRIPTION OF THE DRAWINGS

The embodiments of this disclosure are illustrated by way of example and not limitation in the figures of the accompanying drawings, in which like references indicate similar elements and in which.

Other features of the present embodiments will be apparent from the accompanying drawings and from the detailed description that follows.

DETAILED DESCRIPTION

Disclosed are a method, a device, and a system of efficient confirmation of maximizing patient referral outcome through healthcare utilization and/or referral record evaluation. Although the present embodiments have been described with reference to specific example embodiments, it will be evident that various modifications and changes may be made to these embodiments without departing from the broader spirit and scope of the various embodiments.

Figure 1:
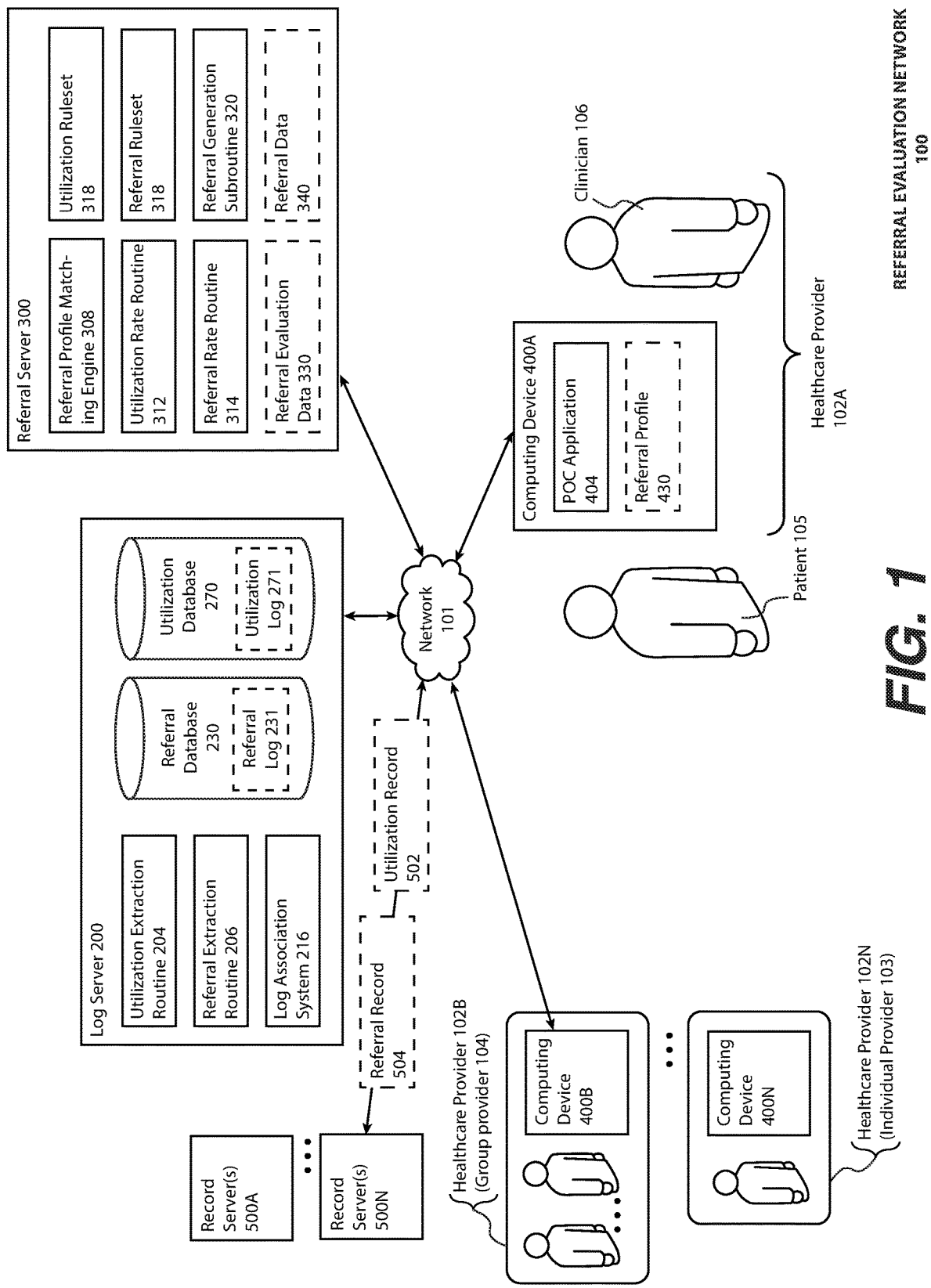
FIG. 1 illustrates a referral evaluation network comprising one or more healthcare providers generating referral records and/or utilization records stored on one or more record servers, a log server extracting and structuring utilization logs (which may also referred to as healthcare utilization logs) and/or referral logs (which may also be referred to as healthcare referral logs) from the utilization records and/or referral records, a computing device of a healthcare provider (acting as a referring provider) to generate a referral request and a referral profile, a referral server generating evaluation data based on a match of the referral profile to a set of the utilization logs and/or referral logs, resulting in generation of actionable referral information for a clinician and/or the patient during a referral process, and a network, according to one or more embodiments.

FIG. 1 illustrates a referral evaluation network, according to one or more embodiments. Instances of a healthcare provider 102, shown as the healthcare provider 102A through the healthcare provider 102N, may provide healthcare services to instances of the patient 105. In one or more embodiments, one or more of the healthcare providers 102 may be within a healthcare network, for example an HMO or ACO. In the course of providing a healthcare service to a patient 105, a healthcare provider 102 may generate a utilization record 502, for example an insurance claim that can be analyzed for information about the healthcare services provided to the patient 105 (e.g., the healthcare claim record 541 of FIG. 5). In the course of making a referral for the patient 105, a first instance of a healthcare provider 102, referred to as a "referring provider," may generate a referral record 504. The referral record 504, for example, may be a referral report generated when a referral is made through scheduling software of the healthcare network. Referral records 504 and/or utilization records 502 are communicated over a network 101 and stored on one or more instances of a record server 500, shown as the record servers 500A through 500N. The record server 500A, for example, may include a claims database 540, as further shown and described in the embodiment of FIG. 5. An instance of the record server 500 may also store additional data, for example a patient EMR database 520, storing data usable in generating logs that can be evaluated to determine value of healthcare services and/or patient 105 access to a healthcare provider 102. The network 101 may be a local area network (LAN), a virtual private network (VPN), a wide area network (WAN), and/or the Internet.

A log server 200 extracts data from records, generates logs (e.g., a utilization log 271 and a referral log 231), and may associate the logs where such associations are identified that associates the logs. A utilization extraction routine 204 extracts data from the utilization record 502, which the log server 200 stores in a utilization log 271 within a utilization database 270. Similarly, the log server 200 detects a referral record 504, uses a referral extraction routine 206 to extract data from the referral record 504, and structures and stores a referral log 231 in a referral database 230. The utilization log 271 may also be referred to as the healthcare utilization log 271. The utilization log 271, for example, may store data such as a provider identifier (e.g., the provider UID 532) of a healthcare provider 102 that provided the healthcare services to a patient 105, a place of service value 250 designating a location and/or facility at which the healthcare service was provided, a type of service value 252, a set of patient data (e.g., the patient data 514 of FIG. 5), and/or a set of relation data defining one or more database associations between the utilization log 271 and other logs as shown and described in the embodiments of FIG. 2, FIG. 10, and FIG. 16. The referral log 231, for example, may store data such as a provider identifier of a referring provider, a provider identifier of a referral provider, a type of service value 252, a referral time 254, the patient data 514, and the relation data 260 defining one or more database associations between the referral log 231 and one or more other logs. In one or more embodiments, a set of associated logs may store data related to, modeling, and/or defining an episode of care of the patient 105.

The log server 200 further comprises a log association system 216 which may identify associations between one or more logs, for example between a referral log 231 and a utilization log 271, between a first referral log 231A and a second referral log 231B, and/or between a first utilization log 271A and a second utilization log 271B. Examples of the referral log 231 and the utilization log 271 are shown and described in detail in the embodiment of FIG. 2, and examples of data structures defining associations between two or more logs are shown and described in conjunction with FIG. 10 and FIG. 16.

In the embodiment of FIG. 1, a healthcare provider 102A acting as a referring provider initiates a referral request to refer the patient 105 to an unspecified instance of the healthcare provider 102 as a referral provider. In one or more embodiments, the healthcare provider 102A may generate the referral in a clinical setting, for example at an appointment where a clinician 106 of the healthcare provider 102A is providing consultation and/or treatment to the patient 105. The clinician 106 may initiate the referral request within a point-of-care application 404 (also referred to herein as the POC application 404) running on the computing device 400A. The computing device 400A, for example, may be a desktop computer, a tablet device, a mobile device, or another computer suitable for running the point-of-care application.

The computing device 400A may generate a referral profile 430. The referral profile 430, for example, may include a place of service range 450, a type of service range 452, and a patient data range 456, as shown and described in FIG. 4. The referral profile 430 may be automatically and/or manually generated, for example by asking the clinician 106 questions and/or providing a user interface (UI) workflow for the clinician 106 to assign a type of service range 452, by automatically retrieving patient data from an EMR of the patient 105 (e.g., a diagnosis code), and/or by accommodating manual input while permitting the clinician 106 to ask questions of the patient 105. The referral profile 430 is communicated through the network 101 to the referral server 300.

The referral server 300 receives the referral profile 430 and in conjunction with the utilization logs 271 and/or the referral logs 231 evaluates probable value and/or access of one or more of the instances of the healthcare provider 102B through the healthcare provider 102N to return actionable information and identify potential referral providers for selection by the healthcare provider 102A. Access and/or value may be based on a variety of rates and evaluations described in one or more of the present embodiments. After receiving the referral profile 430 over the network 101, a matching engine 308 may compare the referral profile 430 to a log dataset 290 of one or more utilization logs 271 and/or more referral logs 231. The profile matching engine 308 determines matches within the ranges specified, for example instances of the utilization log 271 having a type of service value 252 within the type of service range 452.

In one or more embodiments, the value and/or access evaluation may be determined with respect to the type of service range 452 and the place of service range 450 specified in the referral profile 430, such that logs within the type of service range 452 and/or the place of service range 450 are utilized to generate a reduced dataset (e.g., the reduced dataset 390 of FIG. 3) which may increase evaluation relevance for a particular instance of the patient 105.

A utilization rate routine 312 can generate utilization rates for each healthcare provider 102 within the reduced dataset that are indicative of value and/or access. However, in one or more embodiments, the utilization rate routine 312 may calculate a rate of usage of each place of service value 250 in providing healthcare services within the type of service range 452 of the patient 105, which may be referred to as POS utilization rate 332 as shown and described in FIG. 3. The utilization rate routine is further shown and described in conjunction with the embodiment of FIG. 3. The output of the utilization rate routine 312 may include the referral evaluation data 330. A utilization ruleset 316 may then be applied to score, rank, qualify, and/or disqualify one or more healthcare providers 102 within the reduced dataset (e.g., the reduced dataset 390 of FIG. 3) to generate the referral data 340 comprising data identifying one or more healthcare providers 102 and optionally additional information such as the referral evaluation data 330.

In addition, or in the alternative, the referral server 300 may also execute the referral rate routine 314 which can generate referral rates for each healthcare provider 102 within the reduced dataset 390 where such referral rates are indicative of value and/or access. In one or more embodiments, the referral rate routine 314 may calculate a rate at which a referral provider (an instance of the healthcare provider 102 who receives a referral) had a referring provider (an instance of the healthcare provider 102 who issues the referral) re-refer the patient 105 within a given timeframe and within the type of service range 452 of the patient 105. Such a re-referral event may be referred to as the inbound re-referral rate 334 as shown and described in FIG. 3. Rather than relying on marketing statements, scheduling software, and/or outdated information, the inbound re-referral rate 334, including in one or more embodiments as may be narrowed by the referral profile 430, may be a strong indicator of good access. The output of the referral rate routine 314 may also be the referral evaluation data 330. The referral ruleset 318 may then score, rank, qualify, and/or disqualify one or more healthcare providers 102 based on the referral evaluation data 330. A hybrid ruleset 319, shown in the embodiment of FIG. 3, may also be applied to both utilization rates and referral rates within the referral evaluation data 330. The utilization ruleset 316, the referral ruleset 318, and/or the hybrid ruleset 319 may also be used to implement priorities of a healthcare network or other organization running the log server 200 and/or the referral server 300. For example, a healthcare provider 102 with low value across many categories and/or types of healthcare services may have its score reduced even where the score would otherwise be higher for the selected referral profile 430 (e.g., to incentivize general performance increase).

The outcome of the utilization ruleset 316, the referral ruleset 318, and/or the hybrid ruleset 319 is the referral data 340 specifying one or more instances of the healthcare provider 102, and optionally their associated scores, ranks, qualification, and/or underlying referral evaluation data 330 or associated visualizations.

The referral data 340 is returned to the healthcare provider 102A over the network 101 to the computing device 400A. In one or more embodiments, the referral data is integrated into the POC application 404, and/or a user interface of a clinical documentation workflow. This delivery, integration, and display may occur without the clinician 106 ever exiting a software workflow after initiating the referral request. From a user experience of the clinician 106, for example, the clinician 106 may have (i) initiated the referral request, (ii) generated and submitted a referral profile 430, and then (iii) received a list of one or more probabilistically high value and/or good access healthcare providers to choose from to refer the patient 105. The healthcare provider 102A, for example through the clinician 106, may select the referral provider from the list of one or more healthcare providers 102 in the referral data 340 (e.g., the healthcare provider 102B). The selection may then be returned to the referral server 300. A referral generation sub-routine may automatically initiate the referral of the patient 105 from the healthcare provider 102A as the referring provider to the healthcare provider 102B as the referral provider. The initiation may include a manual and/or automatic scheduling process.

In one or more alternate embodiments, the computing device 400A may be replaced with a computing device of the patient 105, where the patient 105 may initiate the referral request and/or select a referral provider from the referral data 340. A referral initiated by the patient 105 and a selection of the healthcare provider 102 by the patient 105 is shown and described in conjunction with the embodiment of FIG. 15.

The healthcare provider 102 may be an individual provider 103 or a group provider 104 comprising one or more instances of the individual provider 103. Each healthcare provider 102 includes one or more instances of a clinician 106 licensed to practice medicine and/or provider healthcare services. A clinician may be an individual provider 103. The healthcare service may be, for example, treatment, diagnosis, health evaluations, medical procedures, laboratory testing, medical imaging, diagnostic testing, and/or surgical procedures.

A utilization record 502 may also include a referral report sent to the referring provider by the referral provider following the performance of the referred service, containing such information as the date of service, the type of service performed, and the result of the service. A referral record 504 may also include an order (digital or an electronic scan of paper), a paper record generated at the point of care of the referring provider, and/or data generated during a referral provider intake process. The POC application 404 may be a commercially available point of care software such as AthenaNet or eClinicalWorks.

Figure 2:
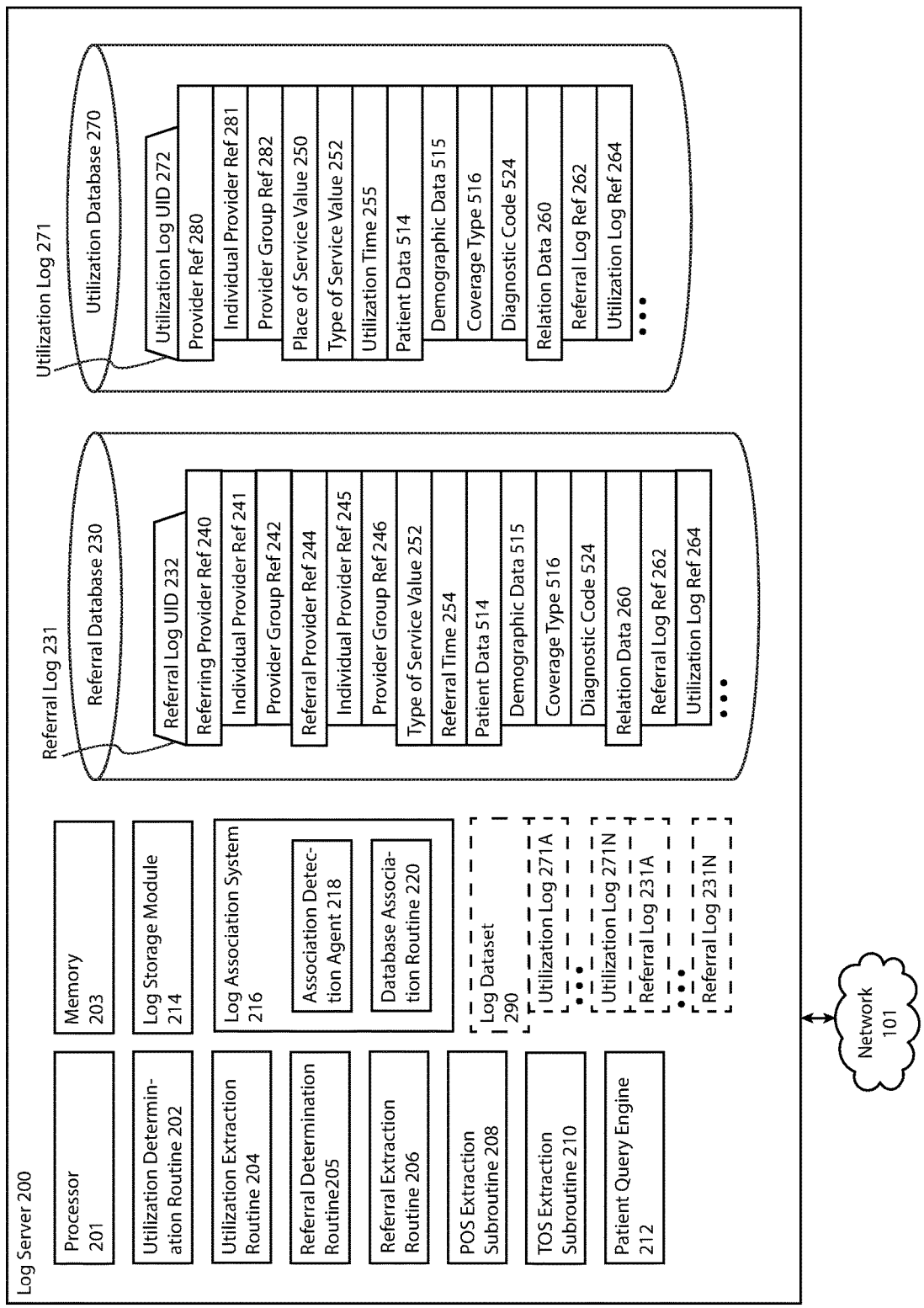
FIG. 2 illustrates the log server of FIG. 1, including a referral database storing one or more referral logs, a utilization database storing one or more utilization logs, a place-of-service (POS) extraction sub-routine for determining a POS value of a location and/or a facility utilized by a healthcare provider in providing a healthcare service, a type of service (TOS) extraction subroutine for determining a type of service value associated with the healthcare service, and a log association system for determining associations between referral logs and/or utilization logs, according to one or more embodiments.

FIG. 2 illustrates a log server 200, according to one or more embodiments. The log server includes a processor 201 that is a computer processor and a memory 203 that is a computer memory, and may further include computer storage (not shown in the embodiment of FIG. 2). The memory 203 and/or the storage may store computer readable instructions of various routines, subroutines, engines, modules, and systems, and may also store the referral database 230 and/or the utilization database 270.

A utilization determination routine 202 comprises computer readable instructions that when executed on a processor determines generation of a utilization record 502 of healthcare services. The utilization record 502 may comprise a patient UID of a patient 105 and a provider UID of a healthcare provider 102 (e.g., associated with providing the healthcare services that the patient 105 utilized). For example, the utilization determination routine 202 may be alerted to a new entry in the EMR 521 of the patient 105, may identify a new record in the claim database 540, or may identify a new referral report received by the referring provider from the referral provider through an electronic link between the electronic health record system (e.g., utilizing a first instance of the EMR database 520A) of the referral provider and the electronic health record system of the referring provider (e.g., utilizing a second instance of the EMR database 520B).

A utilization extraction routine 204 comprises computer readable instructions that when executed on a processor extracts the provider identifier (e.g., a provider UID 532) from the utilization record 502 and initiates collection of data to be transformed into a log. The utilization extraction routine 204 also optionally extracts a set of patient data 256, if available in the utilization record 502, and/or a patient identifier (e.g., a patient UID 512) which may be used to determine additional aspects of the patient data 256. For example, a diagnosis code 524 may be extractable directly from the utilization record 502, whereas the demographic data 515 may need to be queried and returned from the EMR 521 and/or patient profile 511 using the patient UID 512.

A referral detection routine 205 comprises computer readable instructions that when executed on a processor detects a healthcare referral of a patient 105, the healthcare referral from a first healthcare provider 102A (e.g., the referring provider) to a second healthcare provider 102B (e.g., the referral provider). For example, a healthcare referral may be detected by receiving a referral report. In another example, a healthcare referral may be detected when a software code of an EMR management software generates a referral. The detection may even occur manually. For example, following generation of a utilization record 502, the referral detection routine 205 may query a device of the patient 105 and/or the clinician 106 (e.g., through an email, a push notification, a text message) to ask whether the patient 105 was referred, and if so by which healthcare provider 102 acting as a referring provider.

A referral extraction routine 206 comprises computer readable instructions that when executed on a processor extracts the provider UID 532 of the referring provider, the provider UID 532 of the referral provider, and initiates collection of data to be transformed into a log. The utilization extraction routine 204 also optionally extracts a set of patient data 256, if available in the referral record 504, and/or a patient UID 512 which may be used to determine additional aspects of the patient data 256. For example, a diagnosis code 524 may be extractable directly from the utilization record 502, whereas the demographic data 515 may need to be queried from the EMR 521 and/or patient profile 511 using the patient UID.

A POS extraction subroutine 208 comprises computer readable instructions that when executed on a processor determines the place of service value 250 (which may also be referred to as the POS value 250) associated with the utilization record 502. In one or more embodiments, the POS value 250 may be a place of service code value maintained by the Centers for Medicare & Medicaid Services (CMS) of the United States Department of Health and Human Services, which may be two-digit codes placed on health care claims to indicate the setting in which a service was provided. Place of service code values maintained by CMS may be referred to herein as the CMS POS codes. The CMS POS code may be extracted from a healthcare claim 541. In one or more other embodiments, the place of service value 250 may be inferred, for example where a provider profile 531 is associated with a single location and/or facility where the provider could have performed the healthcare service and/or where certain insurance reimbursement codes may implicate a certain place of service (e.g., an emergency service, an imaging system only available at a certain facility, etc.). In another example, a place of service code may be inferred because the type of service is capable of being performed in one place of service only (for example, an "inpatient hospital stay" service is definitionally performed in a hospital). In yet another example, a place of service may be inferred from a facility claim (e.g., which may include a fee for utilizing the facility) that may be associated with a professional claim (e.g., which may include a fee for having received services, treatment, or other health care form a professional). In such case, the professional service may be determined to have been rendered at the place of service. The association may be determined, for example, by comparing a name of the patient 105 and a date on which the service was rendered in both the professional fee and the facility fee.

A TOS extraction subroutine 210 comprises computer readable instructions that when executed on a processor determines that one or more instances of a type of service value 252 associated with the utilization record 502 and may extract and store the one or more instances of the type of service value 252. For example, the TOS extraction subroutine 210 may extract a procedure code 548 from a healthcare claim 541. The procedure code 548 may be a code from the Healthcare Common Procedure Coding System (HCPCS) and/or the American Medical Association's Current Procedural Terminology (CPT) and/or the International Statistical Classification of Disease and Related Health Problems (ICD). The TOS extraction subroutine 210 may also employ natural language processing software and/or artificial neural network language processing to determine words associated with healthcare services and match the words against a database of known procedures and services, not shown in the embodiment of FIG. 2. The type of service value 252 may also be identified by a commonly used and/or bespoke grouping of ICD, CPT, or HCPCS codes (for example, a commercial "code grouper" that groups CPT codes for office visits—such as 99210 through 99215).

Figure 5:
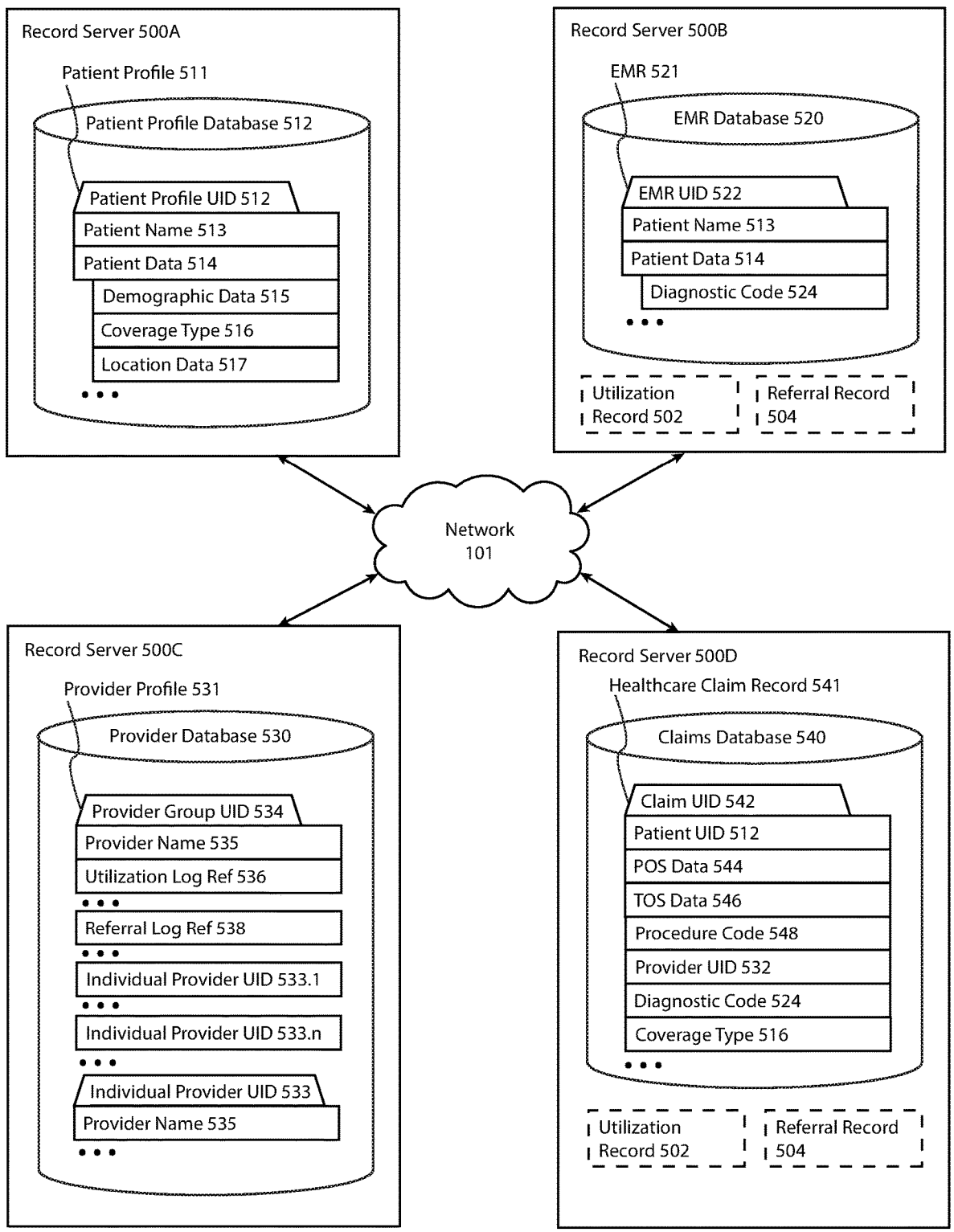
FIG. 5 illustrates one or more records servers housing a patient profile database storing a profile of one or more patients, a provider database storing a profile of one or more healthcare providers, an EMR database having the electronic medical records of one or more patients, and a claims database storing one or more healthcare claims, according to one or more embodiments.

A patient query engine 212 comprises computer readable instructions that when executed on a processor retrieves patient data 514 of a patient profile 511 using a patient UID 512, for example a query against the patient profile database 510 and/or the EMR Database 520 of FIG. 5. The patient query engine 212 may be utilized to add additional patient-related data to the utilization log 271 and/or the referral log 231 such that prospective matching of a referral profile 430 may be made against the patient-related data which may increase evaluation strength. The patient query engine 212 may, for example, retrieve the patient data 256, including the demographic data 515, the coverage type 516, and/or the diagnosis code 524. In one or more embodiments, the patient query engine 212 may not extract or store individually identifiable health information (e.g., which may be known as protected health information, or "PHI"), such that the logs of the log server 200 do not store sensitive and/or government-regulated personal information (e.g., under the Health Insurance Portability and Accountability Act, or "HIPAA"). In one or more other embodiments, the referral log 231 and/or the utilization log 271 may store PHI, including but not limited to the patient UID 512, such that the referral log 231 and/or the utilization log 271 could be expanded with additional patient data 514 at a later time, including in conjunction with a highly specialized instance of the referral profile 430 specifying patient data 514 that is obtainable but not ordinarily stored in the referral log 231 and/or the utilization log 271. In one or more embodiments, a pseudonymous unique identifier may be employed which may aid in associating one or more logs, as described in conjunction with the log association system 216. For example, the patient UID 512 and/or the patient name 513 may be passed into a hash function (e.g., SHA-2) along with a nonce to generate a random and/or unpredictable string to be used as the pseudonymous unique identifier. Although not shown in the embodiment of FIG. 2, the patient profile 511 may also be stored on the log server 200.

A log storage module 214 comprises computer readable instructions that when executed on a processor generates the referral log 231 and/or the utilization log 271 with extracted data from the referral record 504, the utilization record 502, and/or additional retrieved data (e.g., from the patient query engine 212). For example, the utilization log 271 can comprise the provider UID 532 of a healthcare provider 102 (e.g., stored in a service provider ref 280 attribute), the place of service value 250, the type of service value 252, and a utilization time 255 associated with utilization of the healthcare services. The referral log 231 and the utilization log 271 are described in detail below.

A log association system 216 comprises computer readable instructions that when executed on a processor: (i) determines a referral association between a first referral record 504 and/or a first referral log 231 and a second referral record 504 and/or a second referral log 231; (ii) determines an association between a first utilization record 502 and/or a first utilization log 271 and a second utilization record 502 and/or a second utilization log 271; and/or (iii) determines an association between a utilization record 502 and/or a utilization log 271 and a referral record 504 and/or a referral log 231.

The log association system 216 may include an association detection agent 218 comprising computer readable instructions that when executed on a processor determines generation of a log (e.g., the referral log 231 and/or the utilization log 271) and compares the log to other logs within the referral database 230 and/or the utilization database 270 for indicia of association. For example, in one or more embodiments an episode of care may be assigned a unique identifier whereby a patient 105 may be tracked through a health network. In such case the unique identifier of the episode of care may be used to associate logs. In one or more other embodiments, rules-based instructions may be provided, for example determining that two instances of the referral log 231 are each associated with the patient UID 512 (and/or the pseudonymous unique identifier, as described above) were issued within a finite time period from the same referring provider. In another example, an association may be determined between a utilization log 271 that resulted from a healthcare provider 102B and a referral log 231 resulting from a referral of a patient 105 from a healthcare provider 102A to the healthcare provider 102B. In this example, the association may be determined where: (i) a diagnosis code 524 (e.g., a code specifying hip replacement surgery) in the utilization log 271 has a known association to a type of service value 252 (e.g., orthopedic services) in the referral log 231, (ii) where the demographic data 515 of the utilization log 271 and the demographic data 515 of the referral log 231 substantially match (e.g., age, gender, ethnicity), and (iii) where both the utilization log 271 and the referral log 231 are generated within a finite time period (e.g., less than one month, less than six months, less than two years).

The database association routine 220 comprises computer readable instructions that when executed on a processor stores a database association (e.g., a pointer) associating and/or linking at least one of (i) a healthcare utilization log 271 with a referral log 231, and (ii) a referral log 231 (e.g., a referral log 231A) with a healthcare different referral log 231 (e.g., a referral log 231B). The database association routine 220 may define the relation data 260 of the referral log 231 and/or the relation data 260 of the utilization log 271. The pointer may be drawn to a referral log 231 by specifying the referral log UID 232 in the referral log ref 262. The pointer may be drawn to a utilization log 271 by specifying the utilization log UID 272 in the utilization log ref 264. The database association and/or the pointer may be either a one-way or two-way reference and/or link between logs. For example, a referral log 231 may reference a utilization log 271 determined to be associated, but the utilization log 271 may not reference the referral log 231.

A referral database 230 comprises one or more stored referral logs 231. The referral log 231 may also be referred to as a healthcare referral log 231. A referral log 231 comprises a number of attributes and associated values and may be stored on the memory 203 and/or the storage of the log server 200 and/or additional servers. The referral log UID 232 is data uniquely identifying the referral log 231 within the referral database 230. The referring provider ref 240 is an attribute in which the healthcare provider 102 may be specified as the referring provider. In one or more embodiments, the referring provider ref 240 may specify an individual provider ref 241 and a group provider 104 through the provider group ref 242. A data value of the referring provider ref 240, the individual provider ref 241, and/or the provider group ref 242 may be a provider UID 532.

Similarly, the referral provider ref 244 may specify the referring healthcare provider 102. In one or more embodiments, the referral provider ref 244 may specify an individual provider 103 through the individual provider ref 245 and a group provider 104 through the provider group ref 246. The value of the referral provider ref 244, the individual provider ref 245, and/or the provider group ref 246 may be a provider UID 532. An illustrative data structure that may be defined through the referring provider ref 240 and/or the referral provider ref 244 is shown in conjunction with the embodiments of FIG. 10 and FIG. 16.

The type of service value 252 may be one or more values specifying one or more types of healthcare service for which the referral was made. For example, the healthcare service may be broad (e.g., testing, surgery), general (e.g., oncology, medical imaging, trauma, orthopedic surgery), or specific (hip replacement surgery, dialysis services, one or more anticipated procedure codes, etc.). A referral time 254 may be a time and/or a date associated with the referral, for example when the referral was made by the referring provider, timestamped by an information technology system, detected by the log server 200, and/or acknowledged by the referral provider.

The patient data 514 comprises data about the patient 105, which may include demographic data 515, coverage type 516 (e.g., an insurance company and/or other payer covering expenses of the patient 105), one or more instances of a diagnosis code 524, and/or other data retrieved from the patient profile 511 of the patient 105 and/or the EMR 521 of the patient 105. Although not shown in the embodiment of FIG. 2, the patient data 514 may also include the patient UID 512, the patient name 513, and/or the pseudonymous identifier.

The referral log 231 may comprise a relation data 260 relating the referral log 231 to one or more other instances of the referral log 231 and/or one or more other instances of the utilization log 271, as may be defined by the log association system 216.

Figure 3:
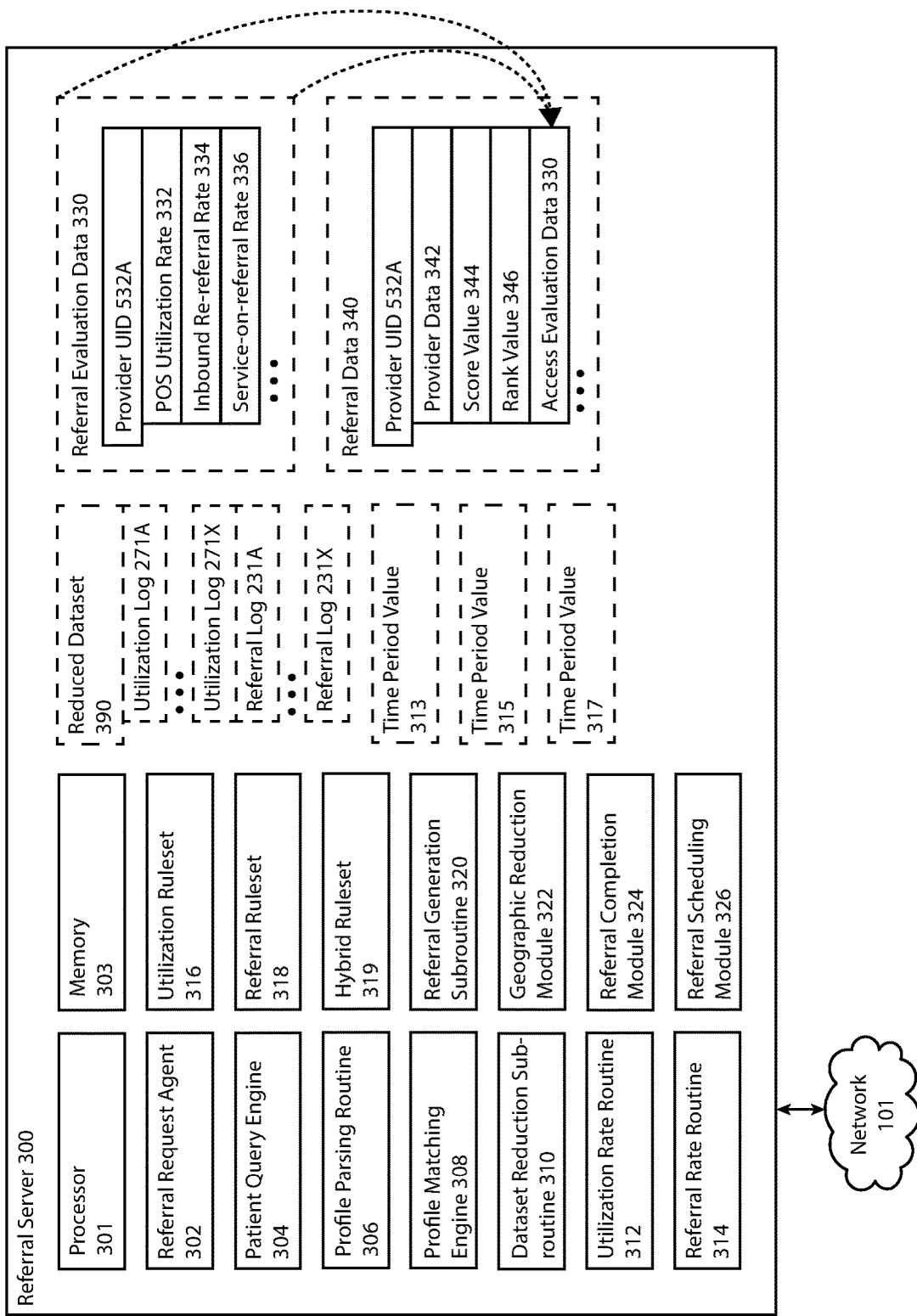
FIG. 3 illustrates the referral server of FIG. 1, including a patient referral profile matching algorithm for comparing the referral profile to one or more utilization logs and/or one or more referral logs, a dataset reduction subroutine, a utilization rate routine for assessing place of service and type of service of a healthcare provider, a referral rate routine for determining detrimental and/or positive referral activity of a healthcare provider, a utilization ruleset, a referral ruleset, and a referral data including one or more healthcare providers determined to score highly, rank highly, and/or or qualify as a referral provider, according to one or more embodiments.

The log dataset 290 may comprise one or more of instances of the referral log 231 (e.g., the referral log 231A through the referral log 231N) that may be usable for referral evaluation such as by the log server of FIG. 3. In one or more embodiments, the log dataset 290 includes every referral log 231 in the referral database 230. However, in one or more other embodiments, the log dataset 290 may be reduced to include less than all of the referral logs 231, for example where only certain instances of the healthcare provider 102 and/or certain time periods are to be evaluated. The log dataset 290 may also be utilized to replicate data from the referral database 230 for portability and/or efficient processing, for example as may be transmitted to the referral server 300 for analysis as shown and described in conjunction with the embodiment of FIG. 3.

The utilization database 270 comprises one or more instances of the utilization log 271. The utilization log 271 may also be referred to as the healthcare utilization log 271. A utilization log 271 comprises a number of attributes and associated values and may be stored on the memory 203 and/or the storage of the log server 200 and/or additional servers. The utilization log UID 272 is data that uniquely identifies the utilization log 271 within the utilization database 270.

The service provider ref 280 is an attribute in which the healthcare provider 102 may be specified as the provider of the healthcare services. In one or more embodiments, the service provider ref 280 may specify an individual provider ref 281 and a group provider ref 282. The data value of the service provider ref 280, the individual provider ref 281, and/or the provider group ref 282 may be a provider UID 532.

A place of service value 250 (which may also be referred to and shown as the POS value 250) may be one or more values specifying a location and/or facility in which the healthcare service was performed, provided, and/or rendered. For example, the place of service value may be based on the CMS POS code values, which may be a set of codes and/or location designators maintained by CMS. However, one skilled in the art will recognize that many other codes, values, and designations are possible, including but not limited to natural language descriptions of locations and facilities.

The type of service value 252 may be one or more values specifying a type of healthcare service for which the referral was made, as described in conjunction with the referral log 231, above. However, the type of service value 252 of the utilization log 271 may also include, for example, procedure codes for procedures, treatments, and/or medical services actually performed. The patient data 514 comprises data about the patient 105, as shown and described in conjunction with the referral log 231, above. Although not shown in the embodiment of FIG. 2, the patient data 514 may also include the patient UID 512, the patient name 513, and/or a pseudonymous identifier. The utilization log 271 may comprise a relation data 260 relating the referral log 231 to one or more other instances of the referral log 231 and/or one or more other instances of the utilization log 271, as may be defined by the log association system 216.

The log dataset 290 may comprise one or more instances of the utilization log 271 (e.g., the utilization log 271A through the utilization log 271N) that may be usable for referral evaluation. In one or more embodiments, the log dataset 290 includes every instance of the utilization log 271 in the utilization database 270. However, in one or more other embodiments, the log dataset 290 may be reduced to include less than all of the utilization logs 271, for example, where only certain instances of the healthcare provider 102 and/or certain time periods are to be evaluated. The log dataset 290 may also be utilized to replicate data from the utilization database 270 for portability and efficient processing, for example as may be transmitted to the referral server 300 for analysis as shown and described in conjunction with the embodiment of FIG. 3. Although not shown in the embodiment of FIG. 2, a hybrid dataset may include both a set of one or more instances of the referral log 231 and a set of one or more instances of the utilization log 271.

Although not shown in the embodiment of FIG. 2, additional databases may be stored on the log server 200 for ease of query in generating the referral log 231 and/or the utilization log 271. For example, a provider database may also be stored (e.g., similar to the provider database 530 of FIG. 3).

FIG. 3 illustrates a referral server 300, according to one or more embodiments. The referral server 300 includes a processor 301 that is a computer processor and a memory 303 that is a computer memory (e.g., RAM, solid state memory). Although not shown, the referral server 300 may include storage (e.g., solid state storage, a hard disk, etc.).

A referral request agent 302 comprises computer readable instructions that when executed on a processor receives a referral request to refer a patient 105 for healthcare services (e.g., over the network 101). The referral request may be initiated by the computing device 400. The referral profile 430 may be generated on the computing device 400 and transmitted to the referral server 300 (as shown in conjunction with the embodiment of FIG. 4), or selections made by the healthcare provider 102 and/or a clinician 106 of the healthcare provider 102 to result in remote and/or server-side assembly of the referral profile 430 (e.g., on the referral server 300).

A profile parsing routine 306 comprises computer readable instructions that validate the referral profile 430, add to the referral profile 430, and/or modify the referral profile 430. The profile parsing routine 306 may also modify the referral profile 430, for example by expanding one or more ranges of the referral profile 430 (e.g., the type of service range 452). The referral request may include a patient UID 512 and an initial instance of the referral profile 430 with a type of service range 452. The patient UID 512 may then be used to query the patient profile 511 to add a patient data range 456 to the referral profile 430 and/or add additional data to the patient data range 456. In one or more embodiments, the components of the patient data range 456 (e.g., the diagnosis code 524) may also be expanded to include additional ranges (e.g., a diagnosis code range that may include similar or related diagnosis codes relevant to the evaluation of value and/or access of referral providers).

A patient query engine 304 comprises computer readable instructions that when executed on a processor queries a patient profile 511 of a patient 105 and/or the EMR 521 of the patient 105 with the patient UID 512 of the patient 105 and then extracts a patient data 514. The patient data 514 may comprise a demographic data 515 of the patient 105, a coverage type of the patient 105, a diagnosis code 524 of the patient 105, and/or other data including but not limited to health data from the EMR 521. The patient data 514 may then be added to the referral profile 430 as the patient data range 456. In one or more other embodiments, the patient query engine 304 may also be present and/or execute on the computing device 400 where assembly of the referral profile 430 occurs on the computing device 400.

The patient query engine 304 may be utilized to complete and/or augment the referral profile 430. For example, as generated by the computing device 400, the referral profile 430 may include a data placeholder for a designation of a coverage type 516 of the patient 105, but the coverage type 516 may not be known by the clinician 106 (or even the patient 105). The patient query engine 212 may then retrieve the coverage type 516 to be added to the referral profile 430. What may be a separate automated process, not shown in the embodiment of FIG. 3, may verify validity of the insurance coverage.

A profile matching engine 308 comprises computer readable instructions that when executed on a processor: (i) compares the referral profile 430 to the set of referral logs 231 (e.g., in the log dataset 290) and to the set of utilization logs 271 (e.g., which may also be included in the log dataset 290), and (ii) determines matching instances of the set of utilization logs 271 and/or the set of referral logs 231 to the referral profile 430. In one or more embodiments, the referral profile 430 specifies a type of service range 452 and a geospatial location of the patient 105 (e.g., the location data 517 such as a residence, a street address). In such example, each referral log 231 and/or each utilization log 271 will be determined to be a match if both (i) the type of service value 252 is within the type of service range 452, and (ii) the healthcare provider 102 acting as the referral provider (as specified in the referral provider ref 244) and/or the service provider (as specified in the service provider ref 280) is within the geospatial area of the patient 105.

The profile matching engine 308 may be exclusionary and/or have additional complex rules for determining relevant matches between the referral profile 430 and the logs (e.g., the utilization log 271 and/or the referral logs 231). For example, where the type of service range 452 does not return enough matches (e.g., lower than a threshold statistical significance), the type of service range 452 may be expanded to include similar healthcare services or more general categories of healthcare services. The place of service range 450, a time range 454, and the patient data range 456, as shown and described in FIG. 4, may also be similarly expanded. For example, where the demographic data 515 of the patient data range 456 specifies a gender, the gender may be removed from the referral profile 430. In another example, a first instance of a referral log 231 and/or a utilization log 271 that matches the referral profile 430 may also automatically generate a match for one or more other logs with at least one database association to the first instance. Modification of matching is further shown and described in conjunction with the embodiments of FIG. 8 and FIG. 14.

A dataset reduction sub-routine 310 comprises computer readable instructions that when executed on a processor reduces the log dataset 290 to the reduced dataset 390 and stores the reduced dataset 390, unique identifiers of each referral log 231 (e.g., the referral log UID 232) and/or unique identifiers of each utilization log 271 within the reduced dataset 390 (e.g., the utilization log UID 272). The portion of the log dataset 290 retained in the reduced dataset 390 may be the matched portion determined by the profile matching engine 308.

A utilization rate routine 312 comprises computer readable instructions that when executed on a processor calculates, using the subset of utilization logs 271A through 271Z in the reduced dataset 390, a place of service utilization rate 332 (which may be shown and referred to as the POS utilization rate 332') of each healthcare provider 102 acting as a referral provider referenced in a service provider ref 280 and for each instance of the place of service value 250. In what may be a simple example, the reduced dataset 390 may comprise six instances of the utilization log 271, with four instances of the utilization log 271 (e.g., the utilization log 271A through the utilization log 271D) associated with a first healthcare provider 102A providing services (e.g., specified through the service provider ref 280), and two instances of the utilization log 271 (e.g., the utilization log 271E and the utilization log 271F) associated with a second healthcare provider 102A providing services (e.g., specified through the service provider ref 280). The utilization log 271A through the utilization log 271C may have a place of service value 250 specified by the CMS POS code '11', which may designate an office, which may be a location, other than a hospital, skilled nursing facility (SNF), military treatment facility, community health center, state or local public health clinic, or intermediate care facility (ICF), where the health professional routinely provides health examinations, diagnosis, and treatment of illness or injury on an ambulatory basis. The utilization log 271D may have a CMS POS code of '20', which may designate an urgent care facility, which may be a location, distinct from a hospital emergency room, an office, or a clinic, whose purpose is to diagnose and treat illness or injury for unscheduled, ambulatory patients seeking immediate medical attention. The utilization log 271E may have a CMS POS code of '11', and the utilization log 271F may have a CMS POS code of '21', which may designate an inpatient hospital, which may be a facility, other than psychiatric facility, which primarily provides diagnostic, therapeutic (both surgical and nonsurgical), and rehabilitation services by, or under, the supervision of physicians to patients admitted for a variety of medical conditions. In this example, the healthcare provider 102A, for any type of service value 252 within the type of service range 452 identified in the referral profile 430, would have a POS utilization rate 336 of 75% for CMS POS code 11 and 25% for CMS POS code 20. The healthcare provider 102B, for any type of service value 252 within the type of service range 452 identified in the referral profile 430, would have a POS utilization rate 332 of 50% for CMS POS code 11, and 50% for CMS POS code 21. The POS utilization rate 332 of each healthcare provider 102 may be stored in the referral evaluation data 330 in association with the provider UID 532. As shown and described in conjunction with the embodiment of FIG. 16, the POS utilization rate 332 may be calculated for each group provider 104 and for each individual provider 103 within the group provider 104. Although what may be a simple example is provided, there may be hundreds, thousands, or more instances of the healthcare provider 102 within the reduced dataset 390, and each instance of the healthcare provider 102 may have associated hundreds, thousands, or more instances of the utilization log 271.

A referral rate routine 314 comprises computer readable instructions that when executed on a processor calculates an inbound re-referral rate 334 and/or a service-on-referral rate 336. The referral rate routine 314 may comprise computer readable instructions that when executed on the processor calculates, using the subset of referral logs 231 within the reduced dataset 390, an inbound re-referral rate 334 of each referral healthcare provider 102 referenced in a referring provider ref 240 and within a time period value 313. The inbound re-referral rate 334 is a rate at which the referring healthcare provider 102 received a first referral and, within the time period value 313, the referring provider issued a second referral to a different referral provider, where the referral log 231 of the first referral and the referral log 231 of the second referral are associated. For example, the referring provider may issue the first referral to the first referral provider. The patient 105 may then be denied service, may receive a price estimate that is too high, and/or the patient 105 may be advised that no appointments are available for a considerable time period (e.g., 2 weeks for an urgent matter, 3 months for a non-urgent matter). The referring provider may then need to re-refer the patient 105 one week later. In what may be a simple example, a healthcare provider 102A may refer a patient 105 to a healthcare provider 102B, resulting in generation of a referral log 231A. The time period value 313 may be two weeks. Twelve days later, the healthcare provider 102A may refer the patient 105 to a healthcare provider 102C, resulting in generation of a referral log 231B. The referral log 231A and the referral log 231B may be associated (e.g., through the relation data 260). In the present example, the healthcare provider 102A would have been subject to a re-referral to be included in calculating the inbound re-referral rate 334. Where the healthcare provider 102A received eight referrals for a type of service value 252 within the type of service range 452 of the referral profile 430, and three of the referrals resulted in re-referrals by the referring provider within the time period value 313, the inbound re-referral rate 334 of the healthcare provider 102 would be calculated at 37.5%.

The inbound re-referral rate 334 may also be calculated with additional information and nuance. In the example above, where the healthcare provider 102A renders service resulting in a utilization log 271 that is associated with the referral log 231A, and the utilization log 271 occurs within a time period value 315 (e.g., one week, one month, six months, two years which may be distinct from the time period value 313), the referral log 231B may indicate a second opinion or even a false positive and/or error in data resulting in generation of an inaccurate instance of the referral log 231B. The time period value may be based on the type of service value 252. The referral rate routine 314, therefore, references the time period value, determines the time associated with generation of the utilization log 271 is within the time period value, and reduces the inbound re-referral rate 334 accordingly. In the example above, where the healthcare provider 102A received eight referrals in which three of the referrals resulted in re-referrals by the referring provider within the time period value 313, but one such re-referral included an associated utilization record 502 and/or utilization log 271 with a second time period value 315, the inbound re-referral rate 334 of the healthcare provider 102 would fall from 37.5% to 25% (two re-referrals out of eight total referrals matching the referral profile 430). Alternatively or in addition, the time assessed may be a time of the actual healthcare utilization, e.g., a time associated with utilization of a healthcare server, as may be recorded in the utilization log 271.

The service-on-referral rate 336 may be the rate at which a healthcare provider 102 directly provides the healthcare service for which the referral was made, within a time period value 317 and for a type of service value 252 within the type of service range 452 of the referral profile 430. For example, a healthcare provider 102 may, acting as a referral provider, receive three referrals from a referring provider resulting in generation of three instances of the referral log 231A through the referral log 231C. Two of the referred patients 105 may either be re-referred by the referral provider and/or not receive healthcare services within the time period value. The third of the referred patients 105 may be provided with healthcare services within the time period, resulting in a utilization log 271 that is associated with (e.g., through the relation data 260) one of the referral logs 231 (e.g., the referral log 231C). In the present example, the service-on-referral rate 336 of the healthcare provider 102 and within all type of service values within the type of service range 452 would be approximately 33.33%.

The referral evaluation data 330 may comprise the output data of the utilization rate routine 312 and/or the referral rate routine 314. The referral evaluation data 330 may include, for one or more instances of the healthcare provider 102A through the healthcare provider 102N (as identified by the provider UID 532A through the provider UID 532N), the POS utilization rate 332 (e.g., for each place of service value 250), the inbound re-referral rate 334, the service-on-referral rate 336, and/or other metrics and rates that may be indicative of value and/or access derivable from the utilization database 270 and/or the referral database 230.

The utilization ruleset 316 comprises a set of rules stored in computer memory (e.g., the memory 303, the storage of the referral server 300) that when applied to the referral evaluation data 330 at least one of scores, ranks, qualifies, and/or disqualifies one or more healthcare providers 102 having a provider UID 532 in the referral evaluation data 330 based on criteria comprising the POS utilization rate 332. The utilization ruleset 316 may store and/or query data associating average cost and/or service quality associated with each instance of the POS value 250. In what may be a simple example, an instance of a POS code value (e.g., CMS code '02' for telemedicine) may be determined to be high ranking, high scoring, and/or qualifying for the given type of service value 252 (e.g., as may be specified in the referral profile 430). Continuing with the present example, each instance of the provider UID 532 within the referral evaluation data 330 may be ranked according to use of the CMS code value equal to '02', with the highest utilization rate ranked highest within the referral data 340. In another example, each provider UID 532 within the referral evaluation data 330 may score (e.g., on a scale of 1 to 5, 1 to 100, Excellent/Good/Fair/Poor, and/or a grade of A to F) based on use of the CMS code value equal to '02'. Although one place of service value 250 has been described, multiple place of service values 250 may be used to generate the score, rank, qualification, and/or disqualification. For example, the provider UID 532 may receive score points equal to the POS utilization rate 332 of the CMS value equal to '02' multiplied by a constant 'x', added together with score points equal to the POS utilization rate 332 of the CMS value equal to '11' multiplied by a different constant 'y'. Ranking may also be made relative to statistical averages within the utilization database 270. In one or more embodiments, a preferred instance of the place of service value 250 may be designed based on criteria comprising the type of service value 252. For example, a given procedure may be specified to be preferred to occur (e.g., based on other cost, value, and/or access metrics and priorities) at a certain CMS code value. A database may be used to define each of such preferred instances of the place of service value 250. It should be noted that the utilization ruleset 316 may also be embodied in computer readable instructions.

A referral ruleset 318 comprises a set of rules stored in computer memory (e.g., the memory 303, the storage of the referral server 300) that when applied to the referral evaluation data 330 at least one of scores, ranks, qualifies, and/or disqualifies one or more healthcare providers 102 having a provider UID 532 in the referral evaluation data 330 based on criteria comprising the inbound re-referral rate 334. It should be noted that the referral ruleset 318 may also be embodied in computer readable instructions. In what may be a simple example, each instance of the healthcare provider UID 532 within the referral evaluation data 330 may be ranked according to the healthcare provider UID 532's associated inbound re-referral rate 334, with a lowest rate of the inbound re-referral rate 334 receiving the highest ranking. In another example, a score may be assigned (e.g., an inbound re-referral rate 334 of less than 10% receives a score of '5' or 'excellent', a score of between 10% but less than 25% receives a score of '4' or 'good', etc.). In another example, each healthcare provider UID 532 may be qualified if it has a calculated instance of the inbound re-referral rate of less than 15%. In yet another example, each healthcare provider UID 532 may be disqualified if it has a calculated instance of the inbound re-referral rate 334 greater than 60%. In another example, each healthcare provider UID 532 may be first qualified, then scored, then ranked. Similarly, the service-on-referral rate 336 may also be scored, ranked, and/or used to qualify or disqualify the provider UID 532.

A hybrid ruleset 319 comprises a set of rules stored in computer memory (e.g., the memory 303, the storage of the referral server 300) that when applied to the referral evaluation data 330 at least one of scores, ranks, qualifies, and/or disqualifies one or more healthcare providers 102 having a provider UID 532 in the referral evaluation data 330 based on criteria comprising the POS utilization rate 332 and at least one of the inbound re-referral rate 334 and the service-on-referral rate 336. For example, an instance of the provider UID 532 may receive a first component of a score from the inbound re-referral rate 334 and a second component of the score from the POS utilization rate 332. Similarly, where a good inbound re-referral rate 334 would otherwise qualify the instance of the provider UID 532, a poor POS utilization rate 332 would be disqualifying. It should be noted that the hybrid ruleset 319 may also be embodied in computer readable instructions.

The referral ruleset 318, the utilization ruleset 316, and/or the hybrid ruleset 319 may also include additional rules that may effect incentives or embody priorities of an operating organization of the referral server (e.g., a healthcare organization). For example, even where an instance of the provider UID 532 may score highly and/or rank highly, additional information about the provider UID 532 may otherwise be disqualifying (e.g., failure to adhere to guideline directed medical therapy). Conversely, where a provider UID 532 may rank poorly, or sufficient data for a ranking and/or scoring may be lacking to be statistically significant, the provider UID 532 may have score and/or rank improvement to ensure a reliable dataset is assembled over time. In one or more embodiments, the qualification and/or ranking may be probabilistic to introduce some randomness into an automated referral provider selection process, e.g., a high score and/or qualification increases the probability the provider UID 532 will be added to the referral data 340. In such case, indications of value and/or access may increase a probability of being presented to a referring provider.

Although not shown in the embodiment of FIG. 3, the provider UID 532 may be further delineated and separately analyzed as a provider group UID 534 and an individual provider UID 533. The referral ruleset 318, the utilization ruleset 316, and/or the hybrid ruleset 319 may be applied for both a provider group UID 534 and/or an individual provider UID 533, with the results averaged or combined as a weighted average. For example, a healthcare provider 102 may be a group provider 104 comprised of four instances of the individual provider 103, an individual provider 103A through an individual provider 103D. The group provider 104 and each of the individual provider 103A through an individual provider 103D may have a distinct inbound re-referral rate 334, service-on-referral rate 336, and POS utilization rate 332 (e.g., resulting in 5 distinctly calculated instances of each rate). The score may be a weighted score, where 50% of the score derives from a score of the provider group UID 534 over the past year, 12.5% of the score of each of the individual provider 103A through the individual provider 103D in the previous six months.

A referral generation subroutine 320 comprises computer readable instructions that when executed on a processor generates a referral data 340 comprising each of one or more instances of the provider UID 532, the provider data 342 (which may include a name of a provider, a street address, and/or other human-readable information), the score value 344, the rank value 346, and/or one or more aspects of the referral evaluation data 330 (e.g., such as the inbound re-referral rate 334, the service-on-referral rate 336, and/or the POS utilization rate 332). One or more instances of the provider UID 532 may be deleted from the referral evaluation data 330, for example due to disqualification. The referral generation subroutine 320 then transmits the referral data 340 over the network 101 to the computing device 400.

A geographic reduction module 322 comprises computer readable instructions that when executed on a processor extract from the patient profile 511 a location data 517 (e.g., a street address, a geospatial coordinate, a postal code) associated with the patient 105 and determines if one or more instances of the healthcare provider 102 are within a predetermined distance (e.g., 5 miles, the postal code, 100 miles of the street address, etc.) based on the location data 517. The location of the healthcare provider 102 may be based on a street address, facility location, etc., as may be queried from the provider profile 531. One or more instances of the provider UID 532 may be further lowered in rank, lowered in score, provided with an "out of range" designation within the referral data 340, and/or disqualified and removed from the referral data 340.

A referral completion module 324 comprises computer readable instructions that when executed on a processor receive a selection of a referral provider from the computing device 400. A referral scheduling module 326 comprises computer readable instructions that when executed on a processor optionally schedules an appointment between the patient 105 and the referral provider.

Figure 4:
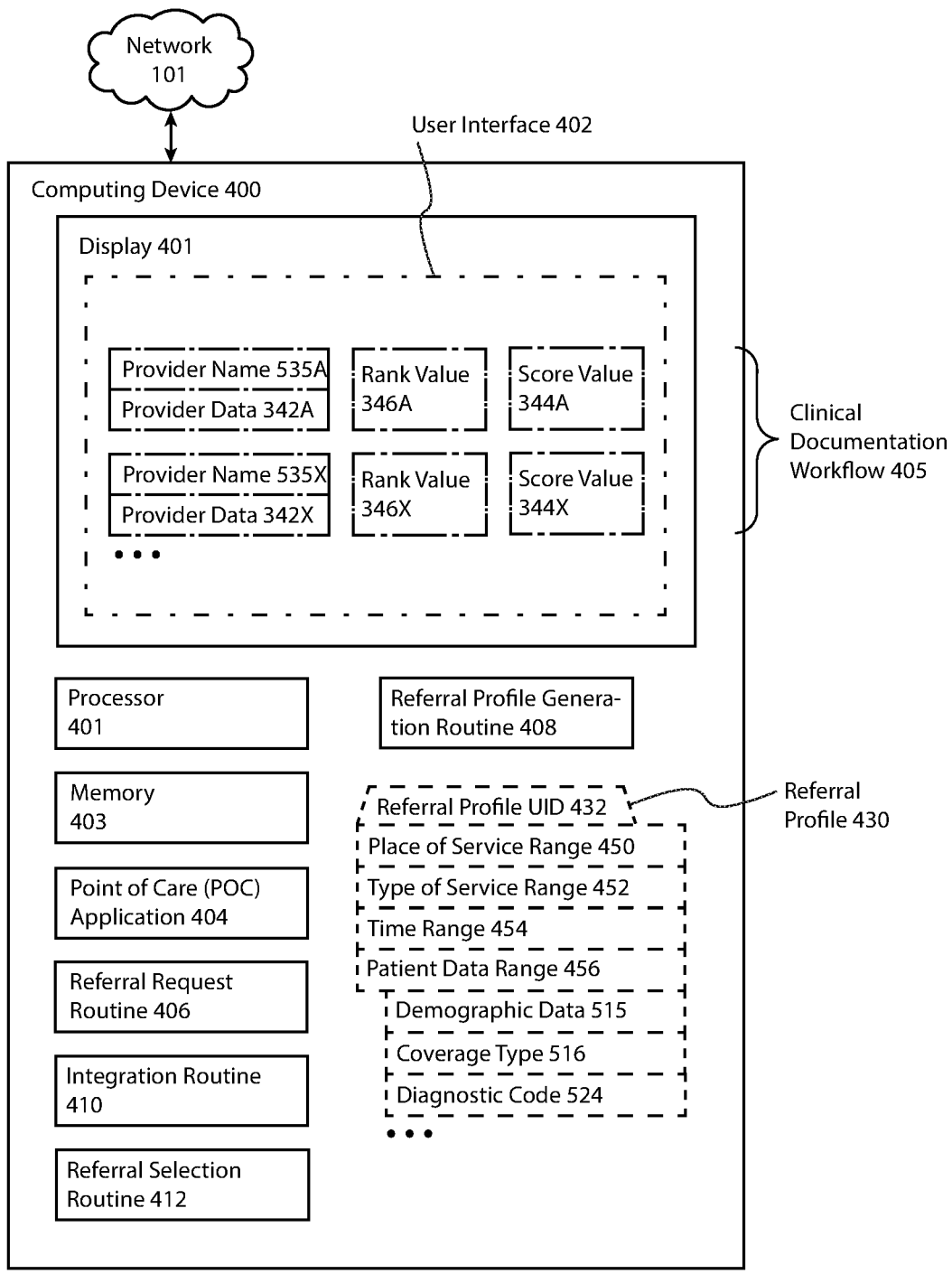
FIG. 4 illustrates a computing device utilized by the healthcare provider who is the referring provider of FIG. 1, including a point-of-care application and clinical documentation workflow for direct interaction between a patient and a clinician, a referral profile generation routine for matching against one or more of the logs of the log server of FIG. 3, and an integration routine for receiving and displaying the referral data, according to one or more embodiments.

FIG. 4 illustrates a computing device 400, according to one or more embodiments. The computing device 400 includes a processor 401 that is a computer processor and a memory 403 that is a computer memory (e.g., RAM, solid state memory). Although not shown, the computing device 400 may include storage (e.g., solid state storage, a hard disk, etc.). A display 401 (e.g., an LCD screen) may display a user interface 402 (e.g., a graphical user interface). A point-of-care application 404 (which may also be referred to as the POC application 404) may be a commercially available software program for treating, diagnosing, and/or otherwise providing healthcare services to a patient 105. The POC application 404 may provide a clinical documentation workflow 405 that includes a workflow for evaluating, diagnosing, documenting, creating care programs for, and otherwise addressing aspects of a health condition. The computing device 400 and/or the POC application 404 may provide the clinician 106 with a user interface 402 for viewing data of an EMR of the patient 105 (e.g., the EMR 521 of FIG. 5), manipulating the clinical documentation workflow 405, and other healthcare functions.

A referral request routine 406 comprising computer readable instructions that when executed on a processor initiates a healthcare referral of a patient 105. The request may be initiated within a clinical documentation workflow 405 of the POC application 404. For example, the clinical documentation workflow 405 may visually and/or graphically identify a condition for which the patient 105 may need treatment. Where a clinician 106 is unable to treat the condition of the patient 105, the clinician 106 may select an option within the user interface 402 to refer the patient 105.

A referral profile generation routine 408 comprises computer readable instructions that when executed on a processor initiates the referral profile 430 within a computer memory (e.g., the memory 303, the memory 403), and stores one or more data ranges in the referral profile 430 where the data ranges are defined automatically and/or through requesting manual input. For example, to the referral profile 430 may be automatically and/or manually added a place of service range 450, a type of service range 452, a time range 454, and/or a patient data range 456 (which may further include a demographic data 515, a coverage type 516, and/or a diagnosis code 524). A manual input may include asking the clinician 106 and/or the patient 105 to input a data value. For example, the clinician 106 may be asked to select a type of service range 452 from a drop-down menu. In another example, the patient 105 may be asked to provide (e.g., within a clinical care setting) one or more aspects of the patient data range 456. Although shown in the embodiment of FIG. 4, the referral profile 430 may be assembled on the computing device 400, the log server 200, and/or other computing devices and servers. Although not shown in the embodiment of FIG. 4, a patient query engine (e.g., operating similarly to the patient query engine 304) may be utilized to query and retrieve data for completing the patient data range 456 from the patient profile 511 and/or the EMR 521. The patient data range 456 may help to determine logs and contextually determine value based on the needs of the patient 105. Alternatively, or in addition, the patient UID 512 may be submitted as part of the referral profile 430 (not shown in the embodiment of FIG. 4) such that the referral profile 430 may be completed, supplemented, and/or modified by the patient query engine 304. The referral profile generation routine 408 may submit the fully or partially assembled referral profile 430 over the network 101 to the referral server 300.

The referral profile 430 includes a referral profile UID 432 and one or more data ranges. A data range may include a place of service range 450, which may be, for example, one or more locations and/or facilities where healthcare services are performed. The place of service range 450 may be designated by one or more CMS POS code values. The place of service range 450 may also include specific locations, for example a specific location and/or facility where healthcare services are provided. The data range may include a type of service range 452, which may include broad categories (e.g., oncology, geriatric medicine, other categories within the Systematized Nomenclature of Medicine (SNOMED)), specific treatments and procedures (e.g., radiation therapy), and/or a set of one or more procedures (e.g., the CPT code values 77427, 77431, 77432, 77435, 77469, and 77470 for radiation therapies), or a specific procedure code value (e.g., CPT code value 77432). The time range 454 may be selected and/or automatically assigned, for example based on the type of service range 452. The time range 454 may be a period in which the set of referral logs 231 and/or the set of utilization logs 271 are relevant. For example, the clinician 106 may be concerned with more recent results (e.g., the last three months) rather than historical value and/or access. On the other hand, it is also possible that the time range 454 may be set by healthcare organization policy (e.g., 6 months), and/or automatically assigned depending on other factors such as the type of service range 452 (e.g., a longer period for cancer treatments, a shorter period for trauma injuries).

The data ranges may include the patient data range 456, which comprises data that may be used to further narrow matches within the log dataset 290 based on characteristics of the patient 105. In one or more embodiments, the patient data range 456 may include a demographic data 515 such as age, gender, ethnicity, location, socio-economic status, employment, education information, income, and/or marital status. The patient data range 456 may include a coverage type 516 that may be an insurance type or other cost coverage type of the patient 105, for example an insurance plan ID, an insurance company name, etc. The diagnosis code 524 may be a medical diagnosis code value (e.g., based on ICD-9-CM, ICD-10, ICPC-2, NANDA, etc.). The patient data range 456 may include many other aspects of additional information and may be drawn from the patient profile 511 and/or the EMR 521. As shown and described herein, the referral profile 430 is submitted by the computing device 400 over the network to the referral server 300.

The ranges specified in the referral profile 430 do not necessarily correspond to the exact patient data 514 and/or the exact healthcare services the patient 105 may need. For example, the type of service range 452 may include services which are not needed by the patient 105 but which are shown to be good indicators of value and/or access for the healthcare service actually needed by the patient 105.

An integration routine 410 comprises computer readable instructions that when executed on a processor receive the referral data 340 within the clinical documentation workflow 405 to provide actionable information to the clinician 106 (e.g., as a clinician 106 of the healthcare provider 102 acting as the referring provider) regarding value and/or access of one or more potential referral providers. In the embodiment of FIG. 4, the referral data 340 is shown in a visual display format on the user interface 402 (e.g., as opposed to a data structure format of FIG. 3). Specifically, in the present embodiment, a list of healthcare providers 102 is displayed, each identified by the provider name 535A through the provider name 535N, and each having provider data 342A through the provider data 342N comprising additional information about the provider such as location, accepted insurance, etc. The provider UID 532 may be included in the referral data 340 transmitted to the computing device 400 (e.g., a provider UID 532A through a provider UID 532N), but may be retained in the memory 403 and not displayed to the clinician 106. In the embodiment of FIG. 4, each instance of the healthcare provider 102 represented within the referral data 340 may also include one or more aspects of the referral evaluation data 330, in this case the rank value 346 and the score value 344 associated with each instance of the healthcare provider 102 represented (e.g., the rank value 346A is the rank of the healthcare provider 102 identified by the provider name 535A).

A referral selection routine 412 comprising computer readable instructions that when executed on a processor receives a selection of a healthcare provider 102 to act as a referral provider. The selection may be made, for example, through the point-of-care application 404 by a clinician 106 of the healthcare provider 102 acting as the referring provider. The selection may comprise the provider UID 532 of the selected referral provider. The selection may be forwarded through the network 101 to the referral server 300 and/or another referral scheduling server.

FIG. 5 illustrates one or more record server(s) 500, according to one or more embodiments. Although the embodiment of FIG. 5 shows distinct instances of the record server(s) 500, two or more of the databases (e.g., the patient profile database 510, the EMR database 520, the provider database 530, and/or the claims database 540) may be stored on the same physical computing server. For example, the patient profile database 510 and the provider database 530 may be stored on the same server of a healthcare organization. Each instance of the record server includes a computer processor 501 that is a computer processor and a memory 503 that is computer memory. Although not shown, the record server 500 may also include computer storage (e.g., a hard disk, a solid state drive). Each instance of the record server 500 are communicatively coupled to the network 101.

The patient profile database 510 comprises one or more instances of a patient profile 511. The patient profile 511 comprises a patient UID 512 which may be a unique alphanumeric string through which the patient 105 may be identified and/or the patient profile 511 addressed, a patient name 513, a coverage type 516 that is an insurance coverage type, a demographic data 515 (e.g., age, gender, ethnicity), and a location data 517, which may be, for example, a geospatial coordinate, an address, a state, a region, and/or a postal code of a residence, a domicile, and/or a place of work, etc.

The EMR database 520 comprises one or more instances of the electronic medical records 521, which may be referred to as the EMR 521. The EMR 521 comprises an EMR UID 522 (which may also be a patient identifier), a patient data 514 which may include data about the patient 105, one or more diagnosis codes 524, and/or additional data related to the patient 105 such as clinical notes, test results, imaging results, reports, evaluations, etc. The EMR database 520 may work in connection with an EMR management application (not shown in the embodiment of FIG. 5), for example, EPIC, Cerner, McKesson, All Scripts, and/or MedSys. One or more records within the EMR database 520 may be sufficient to act as the utilization record 502 and/or the referral record 504.

The provider database 530 comprises one or more instances of a provider profile 531. The provider profile 531 comprises a provider UID 532. In one or more embodiments, the provider profile 531 may be a profile for a group provider 104 or an individual provider 103. Where the provider profile 531 represents a group provider 104, the provider profile 531 may include a reference to each of one or more individual providers 533.1 through 533.n within (e.g., employed by, working for or under) the provider group UID 534. In one or more embodiments, the provider group UID 534 may utilize a tax identification number (TIN) and/or EIN issued by the U.S. Internal Revenue Service. In one or more embodiments, the individual provider UID 533 may be identified through a clinician number or certification number (e.g., a National Provider Identifier (NPI), which may be a unique 10-digit identification number issued to health care providers in the United States by CMS). Although not shown in the embodiment of FIG. 5, additional data related to the healthcare provider 102 may be stored by the provider profile 531, for example the provider data 342 that may be queried (e.g., by the referral server 300) and added to the referral data 340.

The claims database 540 comprises one or more instances of a healthcare claim record 541. The healthcare claim record 541 may comprise a patient UID 512, a set of POS data 544 useable to determine one or more places of service (e.g., and therefore one or more instances of the place of service value 250), a set of TOS data 546 useable to determine one or more types of service (e.g., and therefore one or more instances of the type of service value 252). The healthcare claim record 541 may include a provider UID 532 (including without limitation the provider group UID 534 and/or the individual provider UID 533), one or more instances of a diagnosis code 524, a procedure code 548, and/or a coverage type 516.

Figure 6:
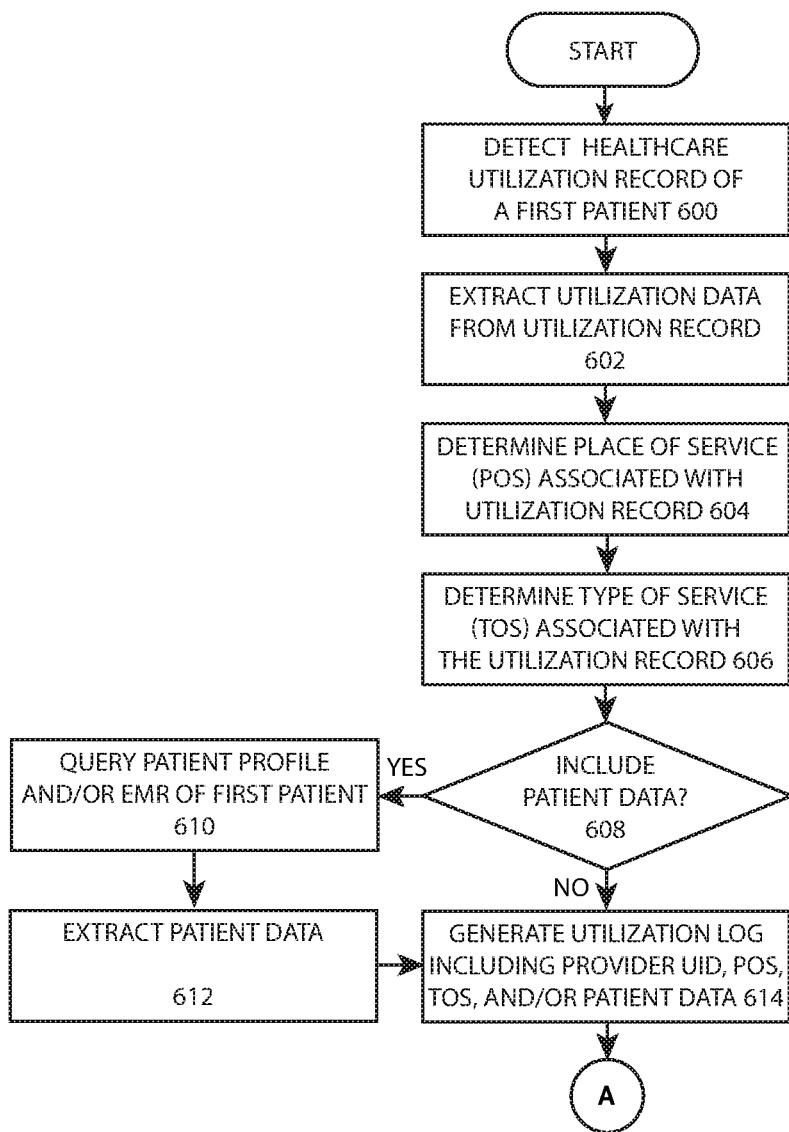
FIG. 6 is a utilization log generation process flow illustrating extraction of utilization data from a utilization record, determination of a POS and TOS associated with the utilization record, augmentation through a patient data (e.g., that may include a demographic data and an insurance coverage type), and storage as a utilization log, according to one or more embodiments.

FIG. 6 is a utilization log generation process flow 650, according to one or more embodiments. Operation 600 detects a utilization record 502 (a record documenting utilization of a healthcare service) of a first patient 105A. For example, a new entry in the EMR 521 of a patient 105 may be stored, a new healthcare claim record 541 may be stored, and/or additional data that may document the provision of healthcare services to the first patient 105 may be determined. Operation 602 extracts utilization data from the utilization record, for example the healthcare provider 102 (as may be later stored in the service provider ref 280 of the utilization log 271), the utilization time 255, and/or one or more aspects of the patient data 514. Operation 604 determines the place of service (POS) value 250 associated with the utilization record 604 (as may be later stored in the POS value 250 of the utilization log 271). The place of service value 250 may be identified as a data field with a two-digit CMS POS code value to be extracted from the utilization record 502.

In another example, the place of service value 250 may be identified as a data field with one or more sub-facilities and/or facility differentiators. For example, the place of service value 250 may be an acuity level (e.g., trauma center designation), an accreditation (e.g., by a private and/or a non-profit organization or a state or a federal agency), a sub-facility having specialized equipment (e.g., an imaging center with an MRI accommodating oversized persons, an infection post-recovery room), and/or a facility funding profile (e.g., a facility which receives federal funding).

Operation 606 determines a type of service associated with the utilization record. For example, operation 606 may extract a procedure code 548 from a healthcare claim 541. In another example, operation 606 may detect one or more predetermined terms, phrases, and/or synonyms from the Healthcare Common Procedure Coding System (HCPCS). In yet another example, operation 606 may employ natural language processing. Operation 608 is a decision determining whether data of the first patient 105 should be gathered for inclusion in a utilization log 271 (including without limitation the patient data 514, the patient name 513, the coverage type 516, the demographic data 515, the location data 517, and/or other information from the patient profile 511 and/or the EMR 521). Where data of the patient is to be included, operation 608 proceeds to operation 610 which queries the patient profile of the first patient 105A (e.g., the patient profile 511) and/or the EMR 521 of the first patient 105A. Operation 612 extracts the patient data 514, and then proceeds to operation 614. If no patient data 514 is to be included at the decision of operation 608, operation 608 proceeds to operation 614. Operation 614 generates a utilization log 271 comprising a provider UID 532, a place of service value 250, a type of service value 252, and/or the patient data (in such case the patient data was extracted and returned in operation 612). Operation 614 may then end, or proceed to the process flow of the embodiment of FIG. 7.

Figure 7:
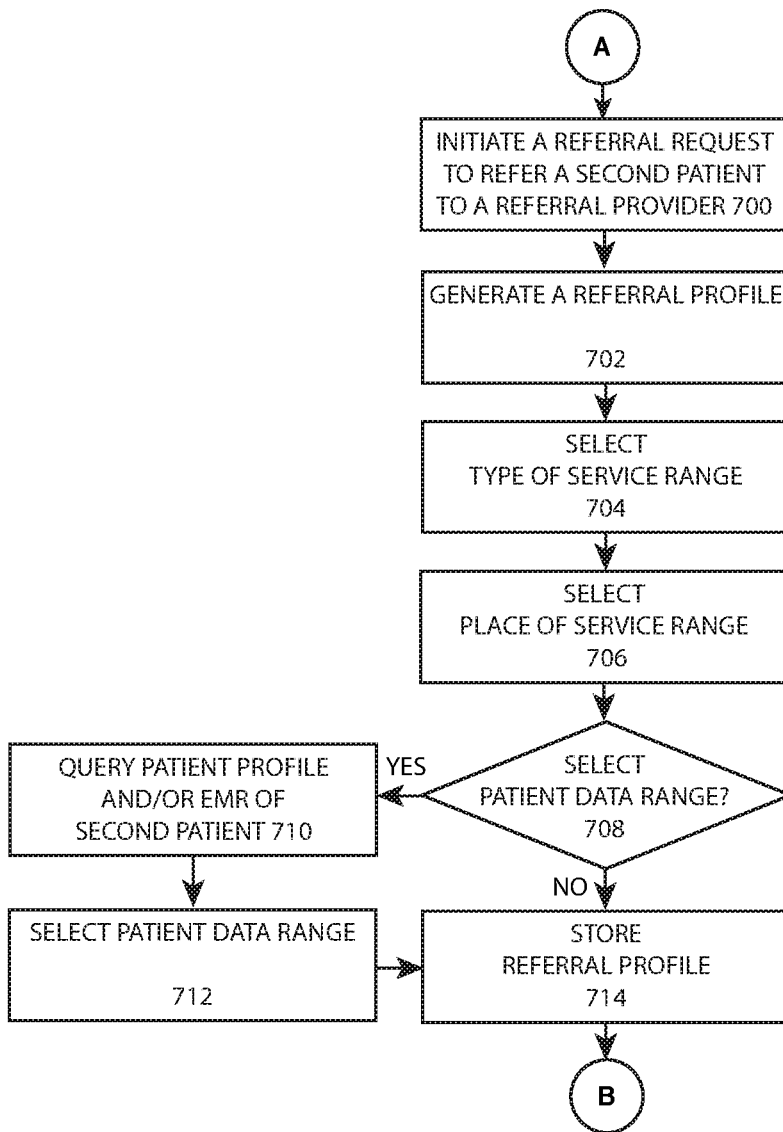
FIG. 7 is a first referral profile generation process flow illustrating initiation and generation of a referral profile, according to one or more embodiments.

FIG. 7 is a referral process generation process flow 750, according to one or more embodiments. Process flow 750 may begin at operation 700 and/or continue operation 614 of process flow 650 of the embodiment of FIG. 6. Operation 700 initiates a referral request to refer a second patient 105B to a referral provider (e.g., a healthcare provider 102 acting as a referral provider). For example, the initiation of the referral request may occur on a computing device 400 through a POC application 404 where the initiator is a clinician 106 and/or through a mobile application where the initiator is the patient 105.

Operation 702 generates a referral profile 430. At the time of generation, the referral profile 430 may be assigned a unique identifier (e.g., the referral profile UID 432) and a set of memory addresses in a computer memory to store additional data of the referral profile 430. Operation 702 may be initiated on a computing device 400, and/or on a computing server (e.g., the referral server 300). Operation 704 selects a type of service range 452 for addition to the referral profile 430. For example, a selection may be received by a trained clinician (e.g., the clinician 106) who may select a healthcare service from a drop-down menu, choose a procedure code from a searchable user interface window or natural language search, etc. In one or more embodiments, the type of service range 452 may be automatically assigned based on activities of the clinician 106 within a clinical documentation workflow 405 of the POC application 404. In the case where the computing device 400 is a device of a patient 105, such as a smartphone, the patient 105 may select the type of service range 452. For example, the patient 105 may select the type of service range 452 with voice recognition interface, a questionnaire leading the patient 105 to select a healthcare service and/or category of healthcare service with a high probability of being correct, etc. Operation 706 selects a place of service range 450 to be stored in the referral profile 430. The place of service range 706 may be two or more places of service, as may be designated with a value (such as a CMS POC code value). For example, the place of service range 452 may specify CMS POC code values '11' (office), '17' (walk in clinics), '20' (urgent care), '21' (inpatient hospital), and '23' (emergency room). In one or more embodiments, all possible places of service (e.g., all CMS POC code values) may be automatically selected as the place of service range 706.

Operation 708 is a decision determining whether a patient data range (e.g., the patient data range 456) should be included in the referral profile 430. If the patient data range 456 is to be included, operation 708 proceeds to operation 710. If not, operation 708 proceeds to operation 714. Operation 710 queries the patient profile 511 of the second patient 105B and/or the EMR 521 of the second patient 105B and gathers data that may include a demographic data 515, a coverage type 516, and/or a diagnosis code 524. Alternatively or in addition, operation 708 may initiate a manual entry process for requesting the clinician 106 and/or the patient 105 to assist in formulating the patient data range 456. Operation 712 selects a patient data range 456 and adds the patient data range 456 to the referral profile 430. Operation 714 stores the referral profile 430 in a computer memory. Although not shown in the embodiment of FIG. 7, an additional process may be the selection of a time range 454 (e.g., one week, six months, five years). Operation 714 may then end and/or proceed to operation 800 of the embodiment of FIG. 8.

Figure 8:
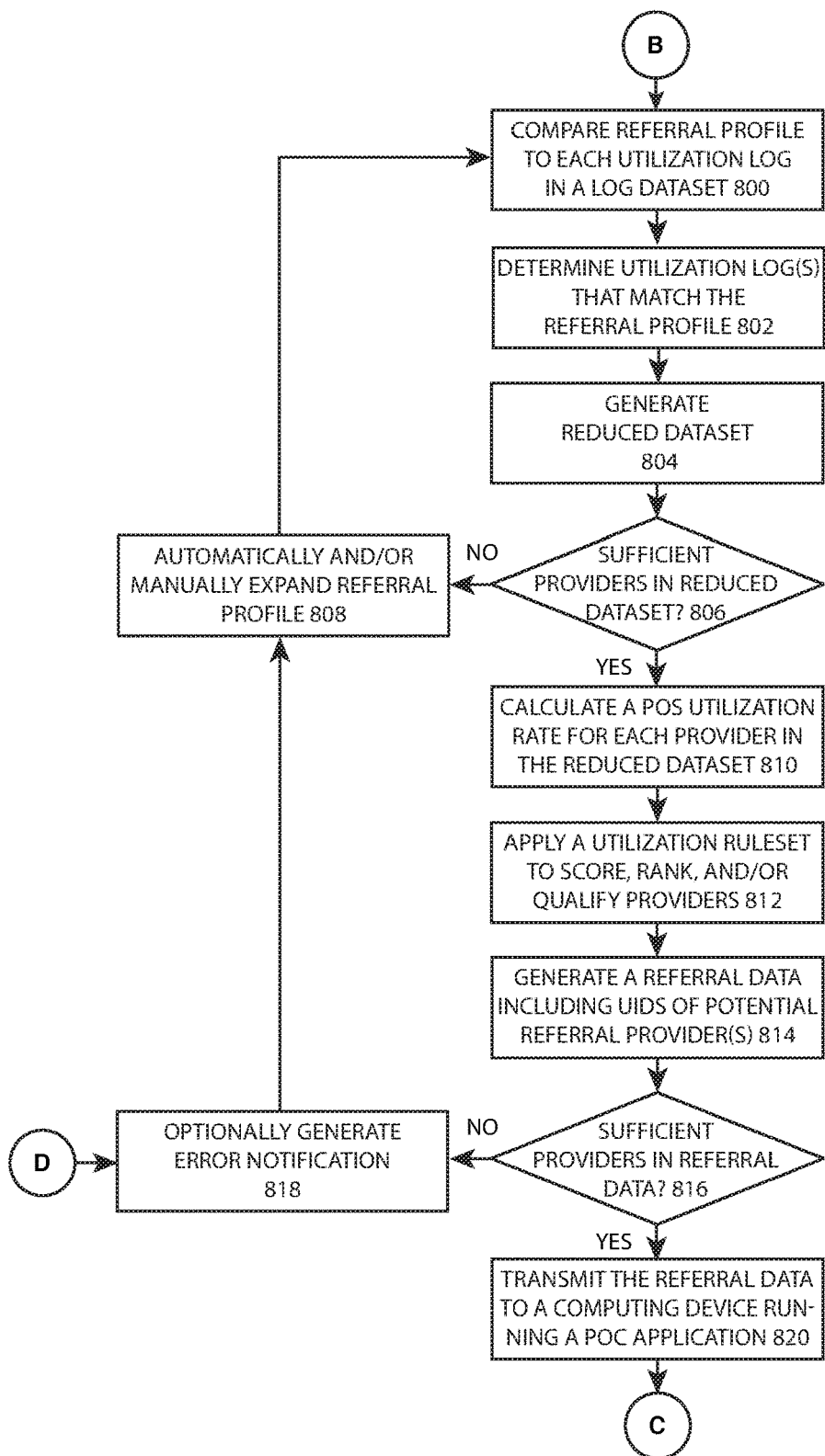
FIG. 8 is a first referral evaluation process flow illustrating matching of the referral profile to one or more utilization logs, generation of a reduced dataset, calculation of one or more POS utilization rates for one or more healthcare providers, application of a utilization ruleset to score, rank, and/or qualify one or more healthcare providers, and generation of a referral data comprising one or more healthcare providers, according to one or more embodiments.

FIG. 8 is a referral evaluation process flow 850, according to one or more embodiments. Operation 800 compares a referral profile 430 to each of one or more utilization logs 271 in a log dataset 290. The log dataset 290 may be stored in a utilization database 230 and/or may be a dataset that is replicated out of one or more databases. Operation 802 determines one or more of the utilization logs 271 match the referral profile 430. In one or more embodiments, the match may need to be exact to be determined as a match. In what may be a simple example, a referral profile 430 may comprise: (a) a type of service range 452 that includes (i) Brain and Neck MRI (e.g., a first instance of the type of service value 252), and (ii) Brain CT (e.g., a second type of service value 252); and (b) a patient data range 456 including a diagnosis code 524 for a cerebral infraction. In such an example, an exact match would be a utilization log 271 in which (a) a type of service value 252 of the utilization log 271 was either "Brain and Neck MRI" or "Brain CT," and (b) the patient data 514 of the utilization log 271 included a diagnosis code 524 for a cerebral infraction. Similarly, in one or more embodiments, more specific matches may be permitted. In the example above, an exact match could also occur where (a) the type of service value 252 of the utilization log 271 was "70460" which may designate a brain CT scan with contrast dye, and (b) the patient data 514 of the utilization log 271 included a diagnosis code 524 of 2015/16 ICD-10-CM I63.40 which may designate cerebral infarction due to embolism of unspecified cerebral artery. However, in one or more embodiments, more general matches may be permitted. In the example above, a match may be determined for a utilization log 271 with (a) any MRI or CT scan healthcare service, and (b) any head or brain-related injury or condition.

Operation 804 generates a reduced dataset (e.g., the reduced dataset 390) comprising one or more instances of the utilization log 271 of the log dataset 290. In one or more embodiments, each of the utilization logs 271 in the reduced dataset 390 may be compressed and/or have extraneous data removed for portability and/or processing efficiency. Operation 806 is a decision for determining whether there are a sufficient number of healthcare providers 102 represented in the reduced dataset 390. For example, a minimum threshold (e.g., three instances of the healthcare provider 102) may be required. In another example, there may need to be a threshold number of healthcare providers 102 with a sufficient data size for analysis (e.g., at least two providers each having at least five matching instances of the utilization log 271). Other data size and sufficiency checks are also possible. If there are a sufficient number of healthcare providers 102 within the reduced dataset 390, operation 806 proceeds to operation 810. If not, operation 806 proceeds to operation 808 which may automatically and/or manually expand the referral profile 808 to be more inclusive (and/or reduce a matching specificity of operation 802). In the above example, the type of service range 452 may be generalized to "MRI healthcare services" and/or a match may be determined for a utilization log 271 with any healthcare service rendered in association with an MRI. Operation 808 may then return to operation 800.

Operation 810 calculates a POS utilization rate 332 for each instance of the healthcare provider 102 within the reduced dataset 390 (e.g., represented in a utilization log 271). Continuing the above example, the POS utilization rate 332 for a first healthcare provider 102A might be 32% in an imaging and radiology center, 40% in a clinical office, and 17% in a hospital, with 11% remaining distributed amongst other categories. A second healthcare provider 102B may have the POS utilization rate 332 of 10% in an imaging and radiology center, 64% in a clinical office, and 5% in a hospital, with 21% remaining distributed amongst other categories.

Operation 812 applies a utilization ruleset 316 to score, rank, and/or qualify each instance of the healthcare provider 102 in the reduced dataset 390 based on criteria comprising the POS utilization rate 332. A score may be a letter score (e.g., A through F), a word score (e.g., good/poor/fair), a number score (e.g., 1 to 100), and/or other scoring methods. The rank may be based on the score, or may be based on the POS utilization rate 332 of one or more categories. For example, each instance of the healthcare provider 102 may be ordered (e.g., by ordering each instance of the provider UID 532A within the referral data 340) first by highest utilization of clinical offices, and second by imaging and radiology center. In one or more embodiments, size and/or quality of each type of facility may also be considered, for example number of MRI machines, types of MRI capabilities, patient volume, number of annual procedures performed, etc. A qualification may be based on certain thresholds (e.g., use of clinical offices greater than 25%, and/or employ Boolean logic (radiology imaging center user %+clinical office use %>hospital use %).

It should be noted that facilities utilized by a healthcare provider 102 may be context specific, for example where certain high-risk patients (e.g., who may be at risk for heart attack, stroke, anaphylaxis to common allergens, may be pregnant, etc.) may have procedures performed in a hospital. The referral profile 430 permits accommodation by selecting such factors as part of the matching criteria (e.g., the diagnosis code 524, which may be unrelated to the service which is being referred). Although not shown in the accompanying figures, an additional risk factor data range may also be logged in the referral log 231 and/or the utilization log 271 and be included in the referral profile 430.

Operation 814 generates a referral data 340 including the UIDs of each potential referral provider (e.g., each instance of the provider UID 532). The referral data 340 may include additional data, as shown and described in conjunction with the embodiment of FIG. 3, including, for example, the POS utilization rate 332. Operation 816 is a decision that determines whether a sufficient number of healthcare providers 102 are within the ranking, qualifying, and/or scoring portion of the referral data 340, and may otherwise operate similarly to operation 806. If a sufficient number of healthcare providers score and/or qualify, operation 816 may proceed to operation 818, which may optionally generate an error notification (e.g., for a clinician 106 and/or an error log for an automated system), then return to operation 808. Alternatively, although not shown in the embodiment of FIG. 8, operation 818 may proceed to an operation which reduces requirements (e.g., qualifications) under operation 812, and/or brings in external factors such as other performance indicators of each instance of the healthcare provider 102. If a sufficient number of healthcare providers 102 in operation 816 are determined, operation 816 proceeds to operation 820 which transmits the referral data 340 to a computing device 400 which may be running a POC application 404 over a network 101. Operation 820 may then end, or proceed to the embodiment of FIG. 9.

Figure 9:
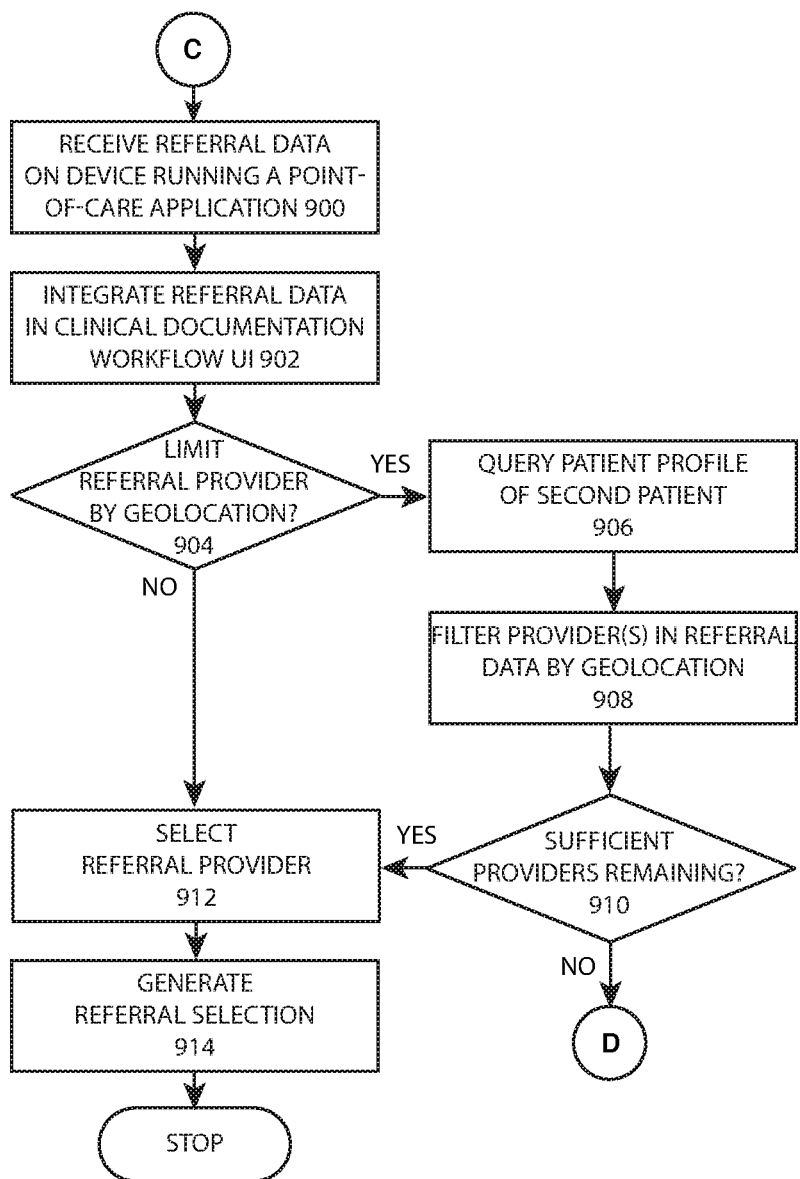
FIG. 9 is a referral selection process flow illustrating receiving referral data on a computing device, integrating the referral data within a clinical documentation workflow, optionally limiting the one or more healthcare providers by geographical area, and receiving a selection of a referral provider, according to one or more embodiments.

FIG. 9 is a referral selection process flow 950, which may begin at operation 900 and/or may continue from the embodiment of FIG. 8. Operation 900 receives a referral data 340 on a computing device 400 running a point-of-care application 404. Operation 902 integrates the referral data 340 in a clinical documentation workflow 405. For example, a user interface window within the clinical documentation workflow 405 may be populated with the top three scoring instances of the healthcare provider 102, with additional instances of healthcare providers 102 within the referral data 340 accessible through a menu, button, or hyperlink. Operation 904 may provide an option to limit providers by geolocation. When selected, operation 904 may proceed to operation 906 which may query the patient profile (e.g., the patient profile 511) of the second patient 105B and retrieve a location data 517 (e.g., a street address, a geospatial coordinate, a postal code) associated the with patient 105. Operation 908 may then determine whether one or more instances of the healthcare provider 102 are within a predetermined distance (e.g., 10 miles, 50 miles, 300 miles) based on the location data 517. For example, operation 908 may filter the one or more instances of the healthcare provider 102 in the referral data 340 by geolocation (e.g., within a distance of the geolocation of the patient 105, within a same postal code, etc.). It will be appreciated by one skilled in the art of computer programming that geospatial filtering may occur in one or more other processes and/or process flows of the present embodiments, and even may be a component of the referral profile 430 (e.g., a location data range, not shown in the figures).

Operation 910 is a decision process that determines whether a sufficient number of instances of the healthcare provider 102 retained in the referral data 340 remain within the geospatial constraint following filtering, for example at least three. If not, operation 910 may generate an error and/or return to operation 818 of FIG. 8. If sufficient healthcare providers 102 do remain for selection, operation 910 proceeds to operation 912. Similarly, where no geospatial limit is selected, operation 904 proceeds to operation 912.

Operation 912 receives a selection of a healthcare provider 102 to be the referral provider. Operation 914 generates the referral selection as data, for example by storing the provider UID 532. The provider UID 523 may be transmitted over the network 101 to one or more services responsible for processing and/or scheduling the referral. A referral log 231 may also be generated in association with operation 914, as shown and described throughout this description.

Figure 10:
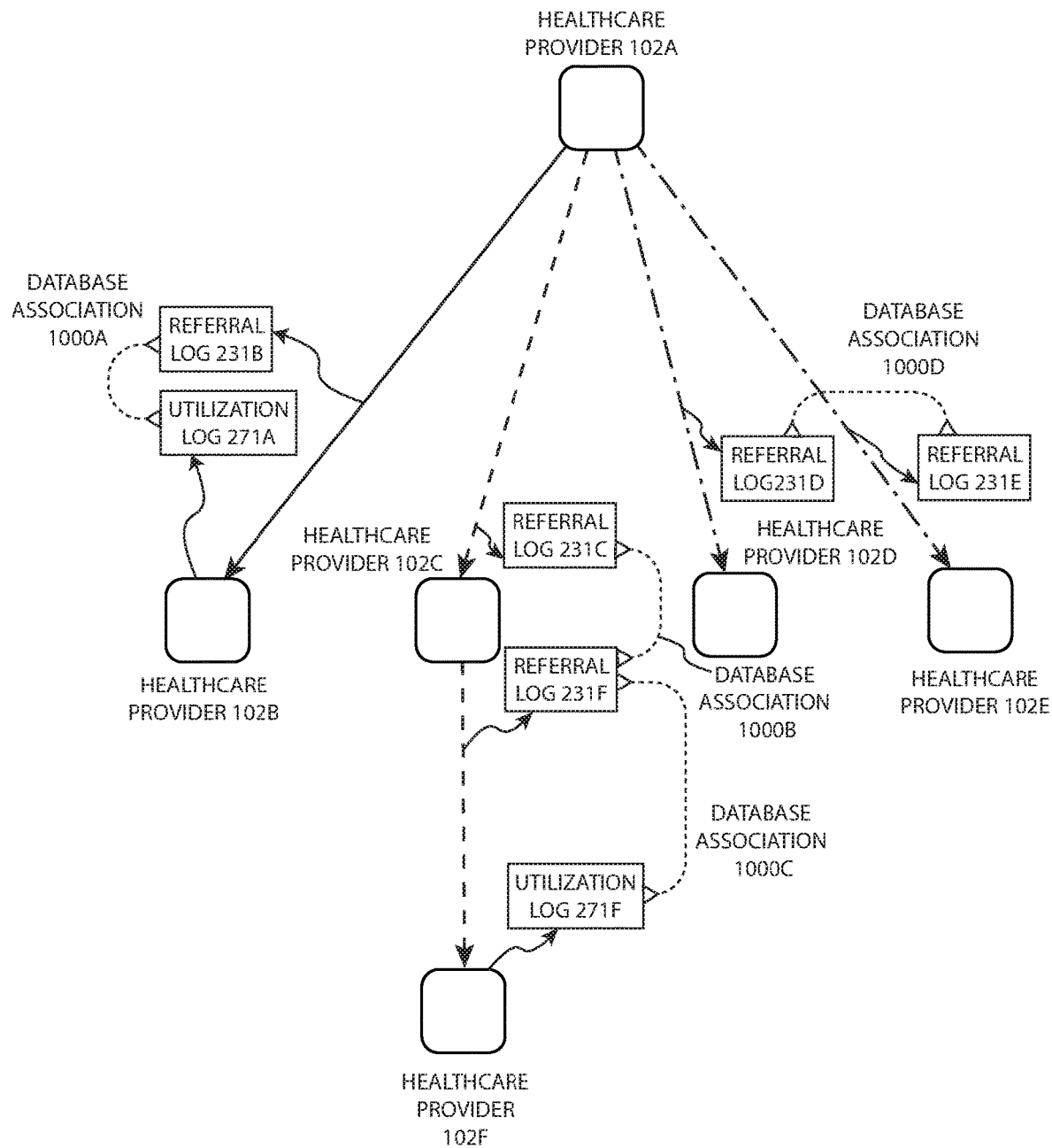
FIG. 10 illustrates a first instance of a log data structure that may be utilized in storing the referral logs and/or the utilization logs of FIG. 2, the log data structure demonstrating database associations defined between related instances of the referral logs and/or the utilization logs, according to one or more embodiments.

FIG. 10 is a log data structure 1050, according to one or more embodiments. In the embodiment of FIG. 10, each square having rounded corners models an instance of the healthcare provider 102A through the healthcare provider 102F. The healthcare provider 102A may refer a patient 105A (not shown) to the healthcare provider 102B, as illustrated by the unidirectional solid arrowed line. The healthcare referral may be documented as the referral log 231B. Subsequently, the healthcare provider 102B may provide services to the patient 105A, resulting in generation of the utilization log 271A. The referral log 231B and the utilization log 271A may be associated (e.g., by the log association system 216 within the relation data 260 of the referral log 231A and/or the relation data 260 of the utilization log 271A). The referral log 231C and the referral log 231F may be associated by a database association 1000B. A rate in which a utilization log 271 becomes associated with a referral log 231 may be an indicator of value and/or access. A time between (i) a referral time 254 of the healthcare referral and/or a time of generation of the referral log 231A, and (ii) a utilization time 255 and/or generation of the utilization log 271A, may be assessed to determine responsiveness and wait time of the healthcare provider 102B.

The healthcare provider 102A may also refer a patient 105B to the healthcare provider 102C as a first healthcare referral along the dashed unidirectional arrowed line running from the healthcare provider 102A to the healthcare provider 102C, resulting in generation of the referral log 231C. In turn, the healthcare provider 102C may refer the patient 105B to the healthcare provider 102F as a second healthcare referral along the dashed unidirectional arrowed line running from the healthcare provider 102C to the healthcare provider 102F, generating the referral log 231F. A time between (i) a referral time 254 of the first healthcare referral and/or a time of generation of the referral log 231C, and (ii) a referral time 254 of the second healthcare referral and/or a time of generation of the referral log 231F, may be assessed to determine responsiveness, wait time, or availability of the healthcare provider 102C. This may be especially indicative where the type of service value 252 is similar or identical in the referral log 231C and the referral log 231F. The healthcare provider 102F may render the healthcare services to the patient 105B, resulting in generation of the utilization log 271F which may then be associated to the referral log 231F through the database association 1000C and/or to the referral log 231C, either by way of the relation data 260 of the referral log 231F or through a direct reference (not shown in the embodiment of FIG. 10).

The healthcare provider 102A may also refer a patient 105C to the healthcare provider as a first healthcare referral along the dot-dashed unidirectional arrowed line running from the healthcare provider 102A to the healthcare provider 102D, resulting in generation of the referral log 231D. The healthcare provider 102A may also refer the patient 105C to the healthcare provider 102E along the dot-dashed unidirectional arrowed line running from the healthcare provider 102A as a second referral to the healthcare provider 102E, resulting in generation of the referral log 231E. In one or more embodiments, a referral pattern may be assessed as a re-referral event where (i) a threshold time is exceeded (e.g., 24 hours) between the referral time 254 of the referral log 231D and the referral time 254 of the referral log 231E, which may indicate both referrals were sequential, and (ii) a second threshold time is not exceeded (e.g., three months), which may indicate that both referrals are still within a same episode of care. In one or more embodiments, where the healthcare provider 102D renders a healthcare service to the patient 105C, even if the referral log 231E has and/or will occur, the referral log 231E in such instance may not be deemed a re-referral but another service utilization (e.g., which may indicate a "second opinion"). Additionally, a time between (i) a referral time 254 of the first healthcare referral and/or a time of generation of the referral log 231D, and (ii) a referral time 254 of the second healthcare referral and/or a time of generation of the referral log 231E, may be assessed to determine responsiveness, wait time, and/or availability of the healthcare provider 102D.

In the embodiment of FIG. 10, although a unidirectional arrow is shown, references may be drawn both backward or forward. For example, the relation data 260 of the referral log 231F may have a referral log ref 262 drawing a reference to the referral log 231C, and the referral log 231C may have a referral log ref 262 drawing a reference to the referral log 231C. Each instance of the healthcare provider 102 shown in FIG. 10 may be further modeled at both a group provider 104 level and an individual provider 103 level, as shown and described in conjunction with the embodiment of FIG. 16.

Figure 11:
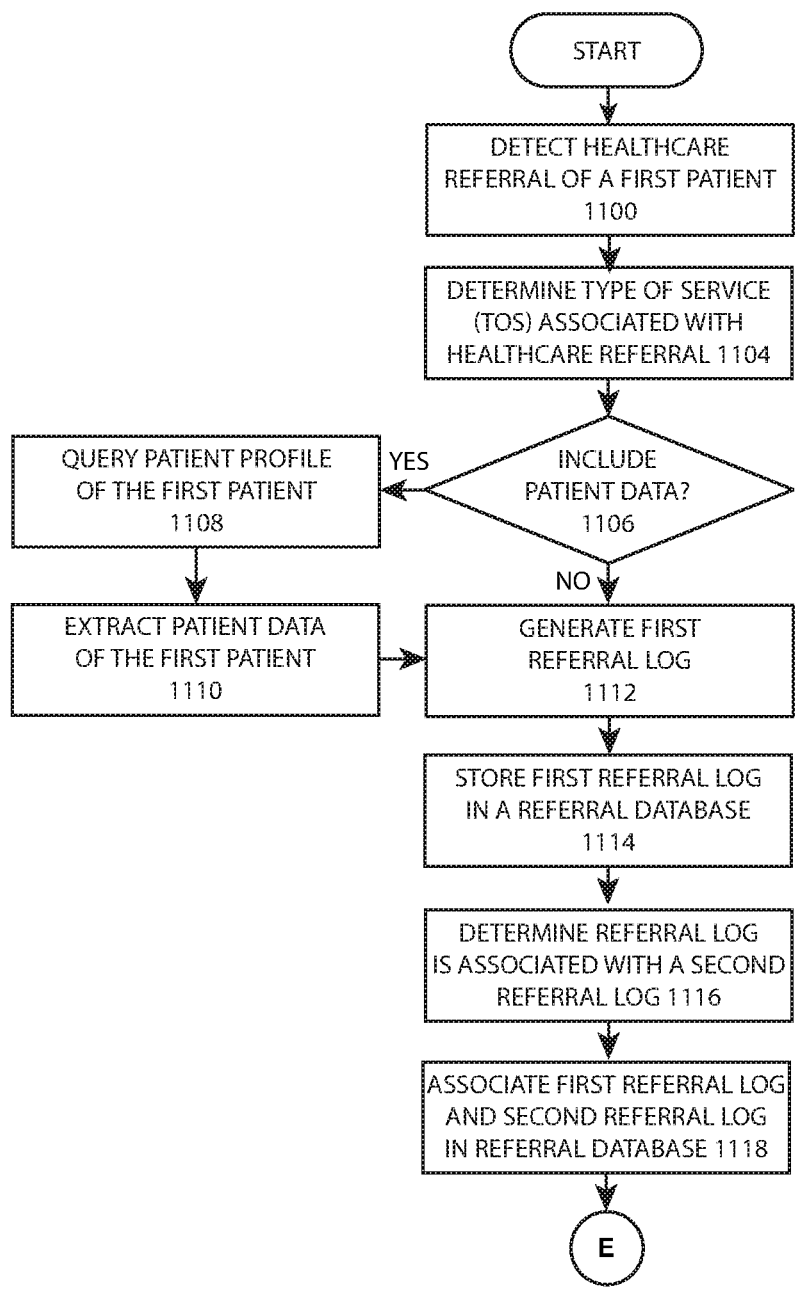
FIG. 11 is a referral log process flow illustrating detection of a healthcare referral of a patient, determination of the TOS value associated with the healthcare referral, storage of a first referral log, determination that the first referral log corresponds to a second referral log, and association between the first referral log and the second referral log (e.g., through the database association of FIG. 10), according to one or more embodiments.

FIG. 11 is a referral log process flow 1150, according to one or more embodiments. Operation 1100 detects a healthcare referral of a first patient 105 (e.g., a patient 105A). The healthcare referral may be detected through identification of a referral record 504, as shown and described in conjunction with the embodiment of FIG. 2. For example, a new entry in the EMR 521 of a patient 105A may be stored, a new healthcare claim record 541 may be stored, and/or there may be stored additional documentary data from which the provision of healthcare services to the patient 105A may be determined. A healthcare referral may also be detected as a result of generating a referral through the process of FIG. 9 and/or FIG. 15.

Operation 1102 determines a type of service (e.g., the type of service value 252) associated with the healthcare referral 1102. Operation 1102 extracts referral data from the referral record 504, for example the healthcare provider 102 acting as the referring provider (as may be later stored in the referring provider ref 240 of the referral log 231). Operation 1102 may also extract the healthcare provider 102 acting as the referral provider (as may be later stored in the referral provider ref 244 of the referral log 231), the referral time 254, and/or one or more aspects of the patient data 514. Operation 1104 determines the type of service (TOS) associated with the utilization record 504 (as may be later stored in the POS value 250 of the referral log 231). For example, operation 1104 may extract a procedure code 548 from a healthcare claim 541. In another example, operation 1104 may detect one or more natural language terms from the Healthcare Common Procedure Coding System (HCPCS). In another example, natural language identification may identify one or more types of service that may be a general (e.g., oncological) and/or more specific (e.g., radiation therapy), or even what may be considered highly specific (stereotactic radiosurgical device surgery, as may be known as Gamma Knife® surgery).

Operation 1106 is a decision determining whether patient data should be gathered for inclusion in a referral log 231 (including without limitation the patient data 514, the patient name 513, the coverage type 516, the demographic data 515, the location data 517, and/or other information from the patient profile 511 and/or the EMR 521). Where patient data 514 is to be included, operation 1106 proceeds to operation 1110 which queries the patient profile of the first patient 105A (e.g., the patient profile 511) and/or the EMR 521 of the first patient 105A. Operation 1110 then extracts the patient data, and then proceeds to operation 1112. If no patient data 514 is to be included at the decision of operation 1106, operation 1106 proceeds to operation 1112. In one or more preferred embodiments, at least some patient data 514 may be appended to the referral log 231, however none is required. In one or more embodiments, a patient UID 512 and/or pseudonymous identifier may be added to the referral log 231 such that the patient data 514 may be added and/or queried at a later time.

Operation 1112 generates a referral log 231 which may comprise a first provider UID 532 for the referring provider, a second provider UID 532 for the referral provider, a type of service value 252, and/or the patient data 514 of the first patient 105A (in such case the patient data 514 was extracted and returned in operation 1110). Operation 1114 may store the first referral log 231 in a referral database (e.g., the referral database 230).

Operation 1112 may then end, or proceed to operation 1114, which may determine the first referral log 231 is associated with a second referral log 231, for example through use of the log association system 216 of FIG. 2. Operation 1118 may then associate the first referral log 231 and the second referral log 231 within the referral database 230, for example by adding a one-way and/or two-way pointer in the first referral log 231 and the second referral log 231 (e.g., the first referral log 231 may link and/or draw an association to the second referral log 231 through the referral log ref 262 of the first referral log 231 and/or the second referral log 231 may draw an association to the first referral log 231 through the referral log ref 262 of the second referral log 231. Operation 1118 may then end, or may proceed to the embodiment of FIG. 12 or the embodiment of FIG. 13.

Figure 12:
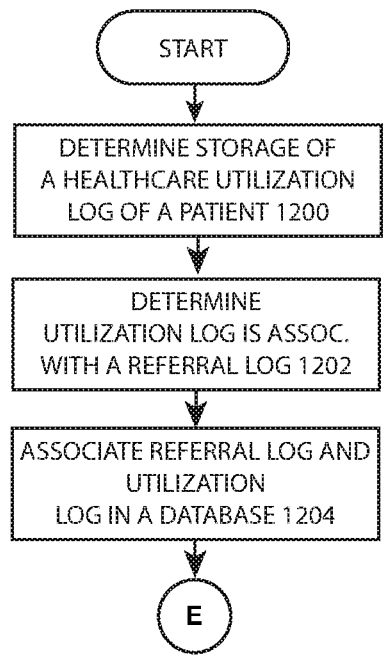
FIG. 12 is a utilization log association process flow illustrating determination of an association between a referral log and a utilization log (e.g., through a database association of FIG. 10), according to one or more embodiments.

FIG. 12 is a utilization log association process flow 1250. Operation 1200 determines storage of a utilization log 271 of a patient 105 (e.g., utilization of healthcare services). Operation 1200 may be triggered and/or execute, for example, upon new storage of the utilization log 271. Alternatively or in addition, operation 1200 may determine storage of a preexisting instance of the healthcare utilization log 271. Operation 1202 determines the healthcare utilization log 1202 is associated with a referral log 1202 (e.g., the first referral log 231 of the embodiment of FIG. 11 and/or the second referral log 231 of the embodiment of FIG. 11). Operation 1202, for example, may utilize the log association system 216 of FIG. 2. Operation 1204 associates the referral log 231 and the healthcare utilization log 271 in a database (e.g., the referral database 230 and/or the utilization database 270). The association may be a one-way or two-way database association made through the relation data 260 of the referral log 231 and/or the relation data 260 of the utilization log 271.

Figure 13:
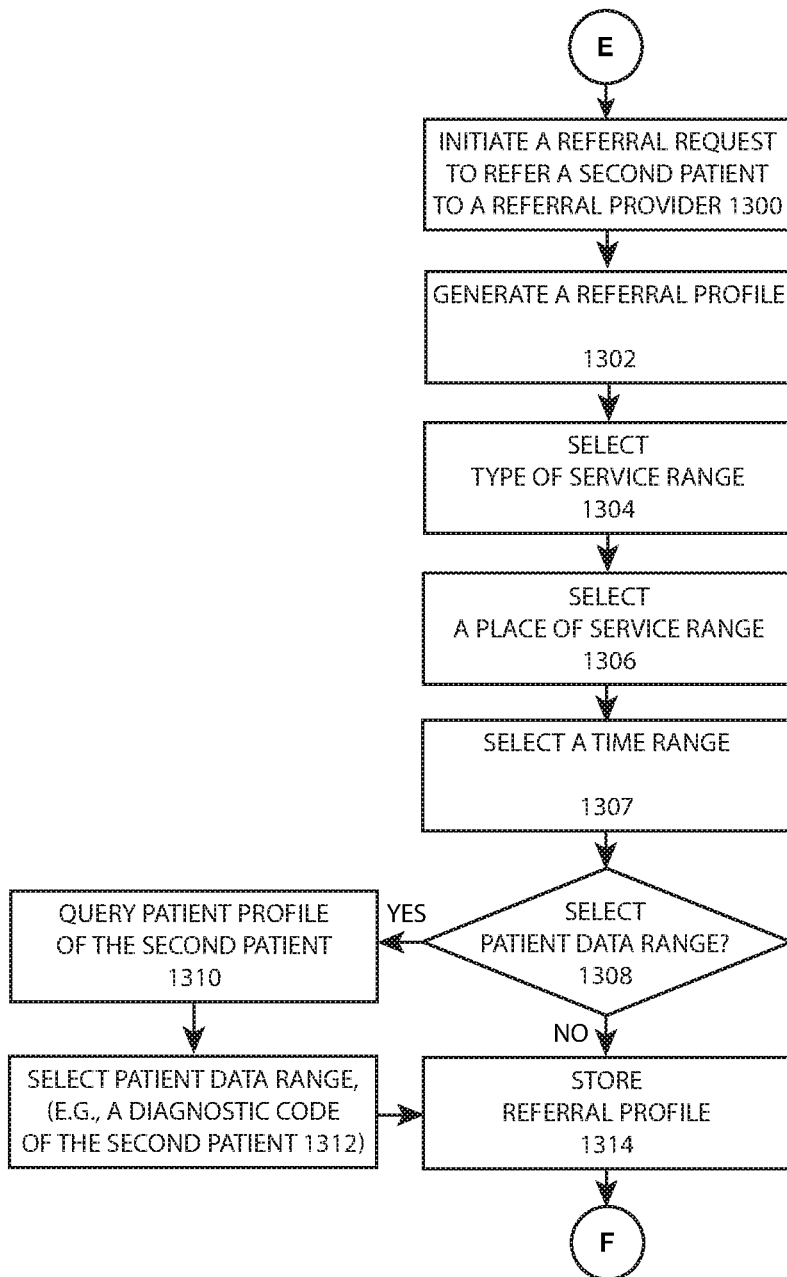
FIG. 13 is a second referral profile generation process flow illustrating initiation and generation of the referral profile, according to one or more embodiments.

FIG. 13 is a referral profile generation process flow 1350, according to one or more embodiments. Operation 1300 may start the process flow 1350 and/or may be a continuation from the embodiment of FIG. 12. Operation 1300 initiates a referral request, and may be similar to operation 700 of FIG. 7. Operation 1302 initiates a referral profile (e.g., the referral profile 430), and may be similar to operation 702. Operation 1304 selects a type of service range (e.g., the type of service range 452). The type of service may include one or more general categories of medical practice (e.g., pediatrics), general categories of healthcare service (e.g., surgical procedures), general categories of procedure (e.g., appendectomy), basic procedure (e.g., procedure code value 44950 for appendectomy), and/or a detailed procedure (procedure code value 44960 for "appendectomy for ruptured appendix with abscess or generalized peritonitis"). Operation 1306 selects a place of service range (e.g., the place of service range 450), and may be similar to operation 706.

Operation 1307 selects a time range (e.g., the time range 454). For example, a clinician 106 may choose (e.g., through the clinical documentation workflow 405) and/or the healthcare organization may automatically preselect a time frame of one month, six months, one year, eight years, all of time for which logs are available, etc., as a matching criteria of the referral profile 430. In one or more embodiments, the time range 454 may be selected based on the type of service range 452 selected (and/or even the patient data range 456 selected in operation 1312).

Operation 1306 then proceeds to the decision of 1308, which, similar to operation 708, determines whether a patient data range 456 should be selected. If a patient data range 456 is to be selected, operation 1306 proceeds to operation 1310. If no aspect of the patient data range 456 is to be included in the referral profile 430 beyond the data already assembled, operation 1308 may proceed to operation 1314. Operation 1308, operation 1310, and operation 1312 may be similar to operation 708, operation 710, and operation 712, respectively. Operation 1314 stores the referral profile (e.g., in the memory 403 of the computing device 400 and/or the memory 303 of the referral server 300). Operation 1314 may then end or proceed to the embodiment of FIG. 14.

Figure 14:
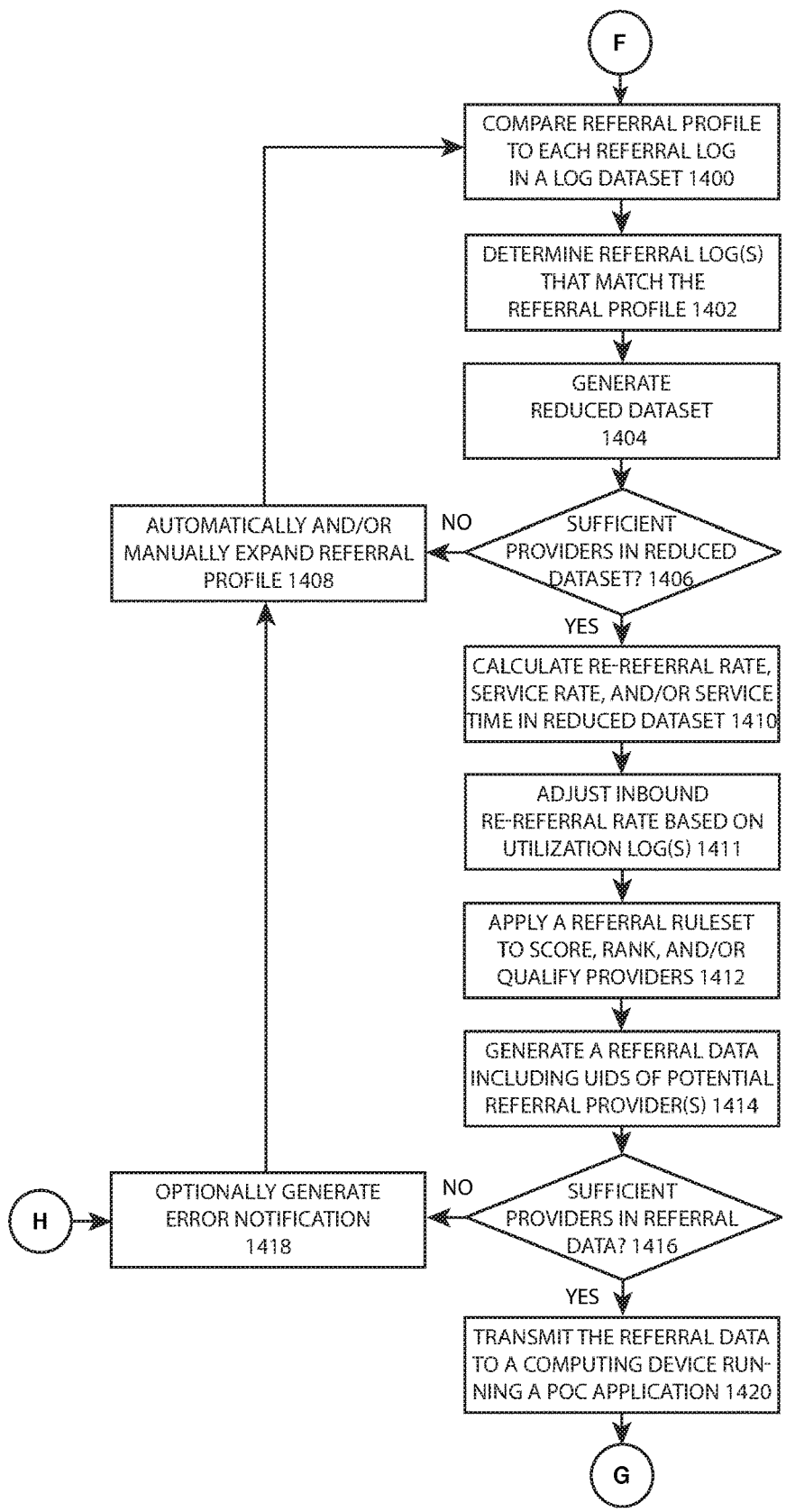
FIG. 14 is a second referral evaluation process flow illustrating matching of the referral profile to one or more referral logs, generation of a reduced dataset, calculation of a re-referral rate, service rate, and/or service time for one or more healthcare providers, and application of a referral ruleset to score, rank, and/or qualify one or more healthcare providers, according to one or more embodiments.

FIG. 14 is a referral evaluation process flow 1450, according to one or more embodiments. Operation 1400 may begin the process flow 1450 and/or may be a continuation of the process flow of FIG. 13. Operation 1400 compares the referral profile (e.g., the referral profile 430) to each referral log (e.g., the referral log 231) in a log dataset 290, where the log dataset includes one or more instances of the referral log 231 (e.g., a referral log 231A through the referral log 231N). Operation 1402 determines one or more instances of the referral log 231 that match referral profile 430. Operation 1402 may be similar to operation 802 of FIG. 8, except to match against the referral log 231 rather than the utilization log 271. In such case, a place of service value 250 or other utilization-based matching criteria may not be used as matching criteria. For the time range 454, a match may be determined where the referral time 254 is within the time range 454. For example, where operation 1402 executes on May 4, and the time range 454 is six months, a match between the referral time 254 and the time range 454 may occur where the referral time 254 specifies a time value on or before December 4 of the previous year. Operation 1404, operation 1406, and operation 1408 may function similarly to operation 804, operation 806, and operation 808 of FIG. 8, respectively. However, the reduced dataset 390 will comprise one or more referral logs 231 (e.g., a referral log 231A through a referral log 231X) rather than (or in addition to) instances of the utilization log 271.

Operation 1410 calculates, from each of the referral logs 231 and/or utilization logs 271 in the reduced dataset 390, an inbound re-referral rate 334 (abbreviated "re-referral rate" in the embodiment of FIG. 14), a service-on-referral rate 336 (abbreviated "service rate" in the embodiment of FIG. 14) and/or a service time (e.g., an average service time). The inbound re-referral rate 334 may calculate, for each referral provider represented in the reduced dataset 390, a rate at which each patients 105 had to be re-referred by a corresponding referring provider. In one or more embodiments, for example, an inbound re-referral may occur for the healthcare provider 102D of FIG. 10 upon generation of the referral log 231E to the healthcare provider 102E. The service-on-referral rate 336 may be determined to be a percentage of the patients 105 of a referral provider for which a utilization log 271 is generated which matches, substantially matches, and/or is otherwise determined to be associated with the referral log 231. For example, in one or more embodiments, the referral to healthcare provider 102B in the embodiment of FIG. 10, including generation of the utilization log 271A, may be considered an instance of service-on-referral. Similarly, the service time may be calculated by comparing the referral time 254 of the referral log 231A and the utilization log 271A, and an average service time calculated.

Operation 1411 may adjust the inbound re-referral rate 334 based on one or more utilization logs 271. For example, returning to the example of healthcare provider 102D of FIG. 10, if the healthcare provider 102D were to generate a utilization log 271 determined to be associated with the referral log 231D within a threshold time period, generation of the referral log 231E may be deemed not to contribute to the inbound-re-referral rate of the healthcare provider 102D. Conversely, although not shown in the embodiment of FIG. 14, it is also possible that where (i) a subject referral provider receives a referral of a patient 105 referral resulting in generation of a referral log 231, (ii) a different healthcare provider 102 provides a healthcare service to the patient 105 resulting in generation of a utilization log 271, and (iii) a match is determined between the referral log 231 and the utilization log 271, then the subject referral provider may, in one or more embodiments, be deemed to be subject to an inbound re-referral.

Operation 1412 applies a referral ruleset 318 to score, rank, and/or qualify each instance of the healthcare provider 102 in the reduced dataset 390 based on criteria comprising the inbound re-referral rate 334, the service-on-referral rate 336, and/or the service time (e.g., an average service time). A score may be a letter score (e.g., A through F), a word score (e.g., good/poor/fair), a number score (e.g., 1 to 100), and based on other scoring methods. The rank may be based on the score, or may be based on a rate value (e.g., the inbound re-referral rate 334, the average service time) of one or more categories. For example, each instance of the healthcare provider 102 may be ordered (e.g., by ordering each instance of the provider UID 532A within the referral data 340) first by lowest inbound re-referral rate 334 and then by highest service-on-referral rate 336. In one or more embodiments, other factors may be considered such as time to re-referral (e.g., which may indicate the healthcare provider 102 that was acting as the referral provider promptly informing the referring provider and/or the patient 105 that no appointment was available). In one or more embodiments, multiple rates can be scored and combined to yield a final score based on multiple factors, for example weighting the inbound re-referral rate 334 as 50% of the score, weighting a POS utilization rate 332 as 25% of the score, weighting a service-on-referral rate as 12.5% of the score, and weighting an average service time as 12.5% of the score.

Operation 1414, operation 1416, operation 1418, and operation 1420 may function similarly to operation 814, operation 816, operation 818, and operation 820, respectively. However, operation 1420 may end and/or proceed to the embodiment of FIG. 15. Although not shown in the embodiment of FIG. 14, operation 1420 may also proceed to the embodiment of FIG. 9.

Figure 15:
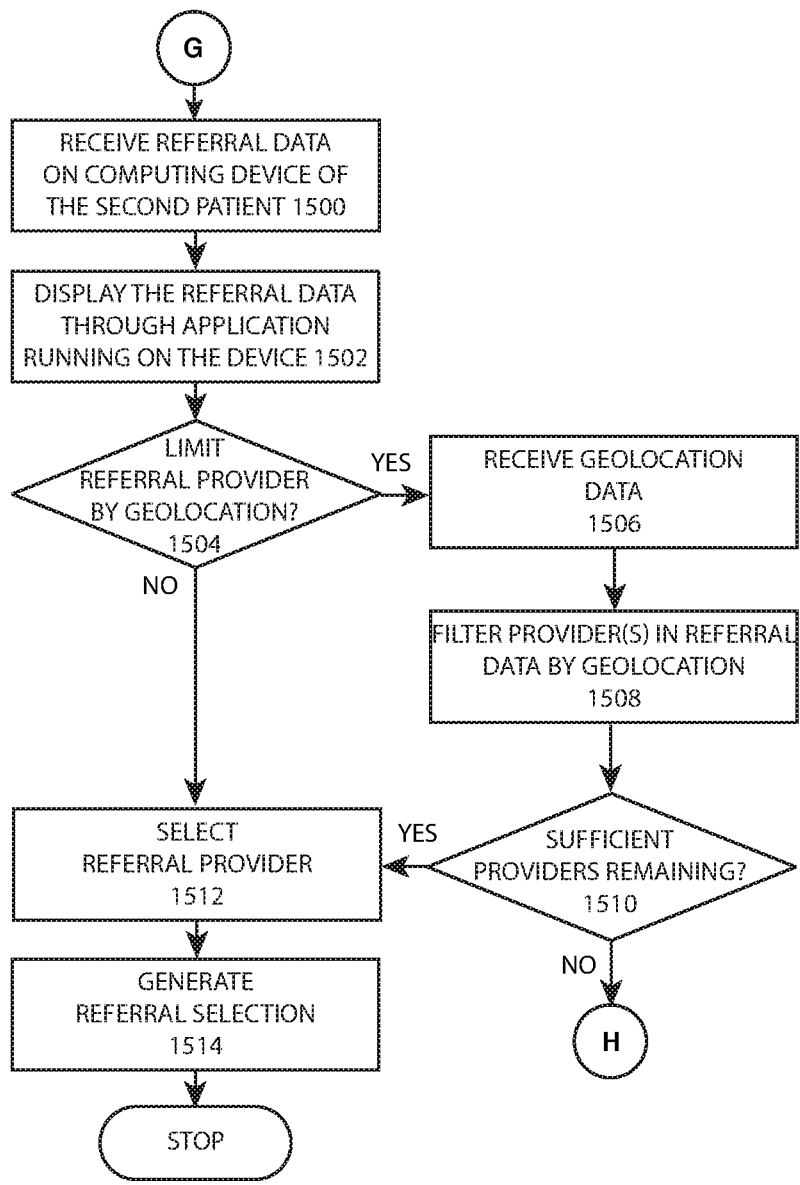
FIG. 15 is a patient selection process flow illustrating selection of a referral provider directly by a patient through a computing device of the patient such as a mobile device (e.g., smartphone), according to one or more embodiments.

FIG. 15 is a patient selection process flow 1550. In the embodiment of FIG. 15, a patient 105 selects the referral provider, for example on a computing device 400 such as a mobile device (e.g., a smartphone), a tablet device, a notebook computer, and/or a desktop computer. Operation 1500 may initiate the process flow of FIG. 15, and/or continue the process flow of FIG. 15 and/or FIG. 8. Operation 1500 receives the referral data 340. For example, the referral data 340 may be received over the network 101 to a computing device 400 of the patient 105 (e.g., continuing the example of FIG. 14, the second patient 105).

Operation 1502 displays the referral data 340 through an application (e.g., a mobile app, a web browser application, a desktop application) running on the computing device 400. For example, the patient 105 may have initiated a referral request in operation 1300 of FIG. 13 through the application, defined one or more aspects of a referral profile 430, and then received the referral data 340 as a result. The referral data 340 may be displayed in a window of the application such that the patient 105 may easily see the name (e.g., the provider name 535), the provider data 342 (including without limitation geographic location and insurance acceptance information), and possibly one or more aspects of the referral evaluation data 330 (e.g., the score value 344, the rank value 346). Operation 1504 may receive a selection (e.g., from the patient 105) to limit and/or organize the one or more healthcare providers 102 within the referral data 340. For example, the patient 105 may have access to a button or filtering option within the application. If limitation based on geolocation is selected, operation 1504 proceeds to operation 1506 where geolocation data is received. For example, the patient 105 may be asked to manually provide geolocation data (e.g., the location data 517 such as a postal code, a street address, approve transmission of a geospatial coordinate from a mobile device and/or an internet protocol (IP) address location, etc.), and/or verify pre-populated data queried from the patient profile 511 (e.g., from the location data 517 which may be queried similar to the process of operation 906 of FIG. 9). Operation 1508 and operation 1510 may operate similar to operation 908 and operation 910, according to one or more embodiments. However, operation 1510 may return to operation 1418 of FIG. 14 where insufficient healthcare providers 102 remain to be selected.

Operation 1512 selects the referral provider, for example by receiving a click, touch, and/or voice input from the patient 105 on the application running on the computing device 400. Operation 1514 generates the referral selection as data, for example by storing the provider UID 532. The provider UID 523 may be transmitted over the network 101 to one or more servers responsible for processing and/or scheduling the referral. A referral log 231 may also be generated in association with operation 1514, as shown and described throughout this description. As a result, the patient 105 (who may be a consumer) may have selected a referral provider with the benefit of support and/or analysis from the referral evaluation data 330. The referral provider may be alerted, a request forwarded, and/or an appointment automatically scheduled.

Figure 16:
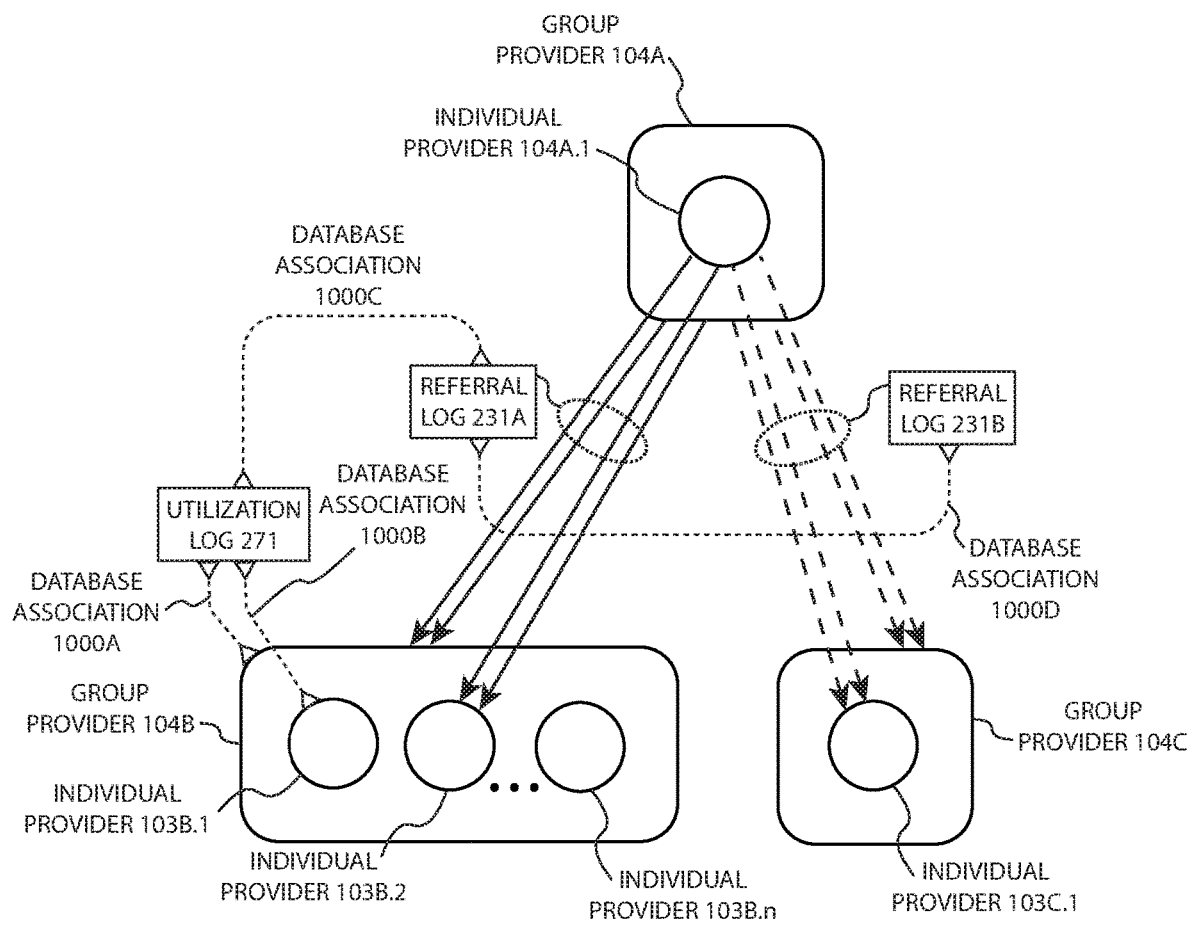
FIG. 16 illustrates a second log data structure in which referral logs and/or utilization logs are associated with both group providers and individual providers within each group provider, according to one or more embodiments.

FIG. 16 illustrates a log data structure 1650, according to one or more embodiments. The embodiment of FIG. 16 illustrates the modeling and storage of data within a data structure in which referral, utilization, and/or other relationships may be tracked and evaluated at a sub-provider level which may increase accuracy and insight into provider value and/or access. A healthcare provider 102 may be an individual provider 103 and a group provider 104. The group provider 104 may be tracked as a business entity (through a business entity ID issued by a state and/or by a business name), a unique taxpayer (e.g., through a tax identification number (TIN) and/or employer identification number (EIN)), etc.), a tracking code assigned by a healthcare organization, and/or another form of unique identifier. The group provider 104 comprises one or more individual providers 103. For example, the group provider 104B comprises 'n' individual providers referred to as the individual provider 103B.1 through the individual provider 103B.n. Although the term "group" is used for the group provider 104, in one or more embodiments the group size may be equal to one, as is shown with the group provider 104A and the individual provider 103A.1. For example, such a group of one instance of the individual provider 103 may be important for tracking later additions to a medical practice initiated by the individual provider 103. The individual provider 103 may be tracked using a tracking ID issued by a government organization (e.g., a National Provider Identifier (NPI), which may be a unique 10-digit identification number issued to health care providers in the United States by CMS).

In the embodiment of FIG. 16, the group provider 104A includes the individual provider 103A.1. The individual provider 103A.1 may make a referral (e.g., through the continuous unidirectional solid line to the group provider 104B, and specifically to the individual provider 103B.2 within the group provider 104B. The referral log 231A may result from such a referral, including up to four documentable relationships: (i) the group provider 104A as a referring provider to the group provider 104B as a referral provider; (ii) the group provider 104A as a referring provider to the individual provider 103B.2 as a referral provider; (iii) the individual provider 103A.1 as the referring provider to the individual provider 103B.2 as the referral provider; and (iv) the individual provider 103A.1 as the referring provider to the group provider 104B as the referral provider. The individual provider ref 241 and the provider group ref 242 may be stored as part of the referring provider ref 240, and the individual provider ref 245 and the provider group ref 246 may be stored as part of the referral provider ref 244, as shown and described in conjunction with FIG. 2.

The utilization log 271 may be associated with both the group provider 104B and the individual provider 103B.1, as shown by the database association 1000A and the database association 1000B in FIG. 16 and which may be stored using the individual provider ref 281 and the provider group ref 282 of FIG. 2. Similarly, the utilization log 271 may be associated with the referral log 231A through the database association 1000C.

Each instance of the healthcare provider 102 may result in evaluated rates and separate but what may be related healthcare value and/or access. For example, a group provider 104 may be responsive and available, while an individual provider 103 may not, and vice-versa. Similarly, an individual provider 103 may move between groups (e.g., be hired by a group, found a new group, etc.). In one or more embodiments, therefore, a measurement of both individual providers 103 and group providers 104 may be combined for what may be more accurate and insightful data related to value and/or access. For example, an inbound re-referral rate 334, a service-on-referral rate 336, and/or a POS utilization rate 332 may be calculated for both a group provider 104 and for an individual provider 103 within the group provider 104. The results may be combined, weighted and combined, or provide additional factors for application of the utilization ruleset 316 and/or the referral ruleset 318. For example, qualification for inclusion in the referral data 340 may require consistency between individual providers 103 within a group provider 104, for example, such that no individual provider 103 has a POS utilization rate 332 for hospitals that exceeds more than twice that of other individual providers 103 within the same instance of the group provider 104. Other data that is possibly insightful may also be identified. For example, where the referral was made to the individual provider 103B.2, the individual provider 103B.1 appears to have performed the associated healthcare service, which may indicate time and/or administrative resources may be saved in direct referral to the individual provider 103B.1 within the same group provider 104B. In the embodiment of FIG. 16, an inbound re-referral is also illustrated through the four unidirectional dashed arrowed lines. If determined to be an inbound referral qualified to increase an inbound re-referral rate 334, the inbound re-referral rate may increase for both the individual provider 103B.2 and for the group provider 104B. Where both the individual provider 103 and the group provider 104 is evaluated, they may be included as distinct entities within the referral data 340, or may be collapsed into a single representation for purposes of the clinician 106 and/or the patient 105 selecting a referral provider. The representation may generally be either the group provider 104 or the individual provider 103 within the group provider 104. Details distinguishing the group provider 104 and the individual provider 103, and their respective score, rank, and/or qualification, may be available through a user interface by selecting an option for more information.

Figure 17:
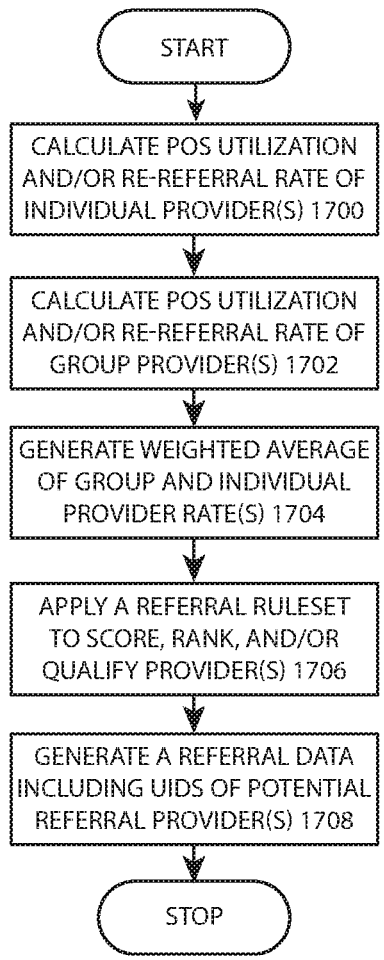
FIG. 17 is a provider evaluation process flow illustrating analysis of the logs of one or more group providers and one or more individual providers to generate a referral data based on a weighted average of re-referral rates, according to one or more embodiments.

FIG. 17 is a provider evaluation process flow 1750, according to one or more embodiments. Operation 1700 calculates a POS utilization rate 332 and/or an inbound re-referral rate 334 of one or more individual providers 103 represented within the reduced dataset 390. An individual provider 103, as shown and described herein, may be represented where one of more of the utilization logs 271 and/or one or more of the referral logs 231 include a reference to the individual provider 103 within the individual provider ref 245 of a referral log 231 and/or the individual provider ref 281 of the utilization log 271. Operation 1702 calculates a POS utilization rate 332 and/or an inbound re-referral rate 334 of one or more group providers 104 represented within the reduced dataset 390. A group provider 104, as shown and described herein, may be represented where one of more of the utilization logs 271 and/or one or more of the referral logs 231 include a reference to the group provider 104 within the provider group ref 246 of a referral log 231 and/or the provider group ref 282 of the utilization log 271. The POS utilization rate 332 and the inbound re-referral rate 334 of both the individual provider 103 and of the group provider 104 may be stored under discrete instances of the provider UID 532 within the referral evaluation data 330, e.g., a provider group UID 534 and an individual provider UID 533.

Operation 1704 applies a weighted average of group provider 104 and individual provider 103 rates (e.g., the POS utilization rate 332 and/or an inbound re-referral rate 334). For example, a weighted instance of the POS utilization rate 332 on which a score and/or rank may be based may be weighted such that 60% comes from the group provider 104 receiving the referral (e.g., in the embodiment of FIG. 16, the solid unidirectional arrow running from the group provider 104A and/or the individual provider 103A.1 to the group provider 104B) and 40% from the comes from the individual provider 103 receiving the referral (e.g., in the embodiment of FIG. 16, the individual provider 103B.1 associated with the utilization log 271 of FIG. 16).

Operation 1706 applies a referral ruleset to score, rank, and/or qualify healthcare providers 102. The referral ruleset may be the utilization ruleset 316, the referral ruleset 318, and/or the hybrid ruleset 319. The referral ruleset may score based on both the POS utilization rate 332 and/or the inbound re-referral rate 334. For example, the referral ruleset may award a score to each group provider 104 based on an inbound re-referral rate 334 of each of the individual providers 103 of the group provider 104. In another example, the referral ruleset may rank primarily by POS utilization rate 332 of the group provider 104, and secondarily by an average of the inbound re-referral rates 334 of each individual provider 103 within the group provider 104. In yet another example, the group providers 104 may be ranked according to the inbound re-referral rate of the group provider 104, but may be disqualified or reduced in rank if any individual provider 103 within the group provider 104 has an inbound rereferral rate exceeding a threshold percentage such as 75%. One skilled in the art will recognize additional possibilities for score, rank, and/or qualification. In one or more embodiments, operation 1704 may be removed and any weighting completed by the referral ruleset of operation 1706.

Operation 1708 generates a referral data 340 including UIDs of one or more potential referral providers, e.g., the provider UID 532. Each instance of the individual provider 103 and each instance of the group provider 104 may be included as distinct entities within the referral data 340, or may be collapsed into a single representation for purposes of human identification and selection, as described in conjunction with the embodiment of FIG. 16. In one or more embodiments, the representation is either a group provider 104 or the individual provider 103. In one or more other embodiments, the group provider 104 may be prominently identified, with the individual provider 103 within the group provider 104 also listed with less visual emphasis. The representation may also differ based on whether the referral data 340 is to be presented to a clinician 106 (e.g., which may wish for more information on the group provider 104) or the patient 105 (e.g., which may wish for more emphasis on the individual provider 103, including a profile photo of each clinician 106 that may be the individual provider 103).

Figure 18:
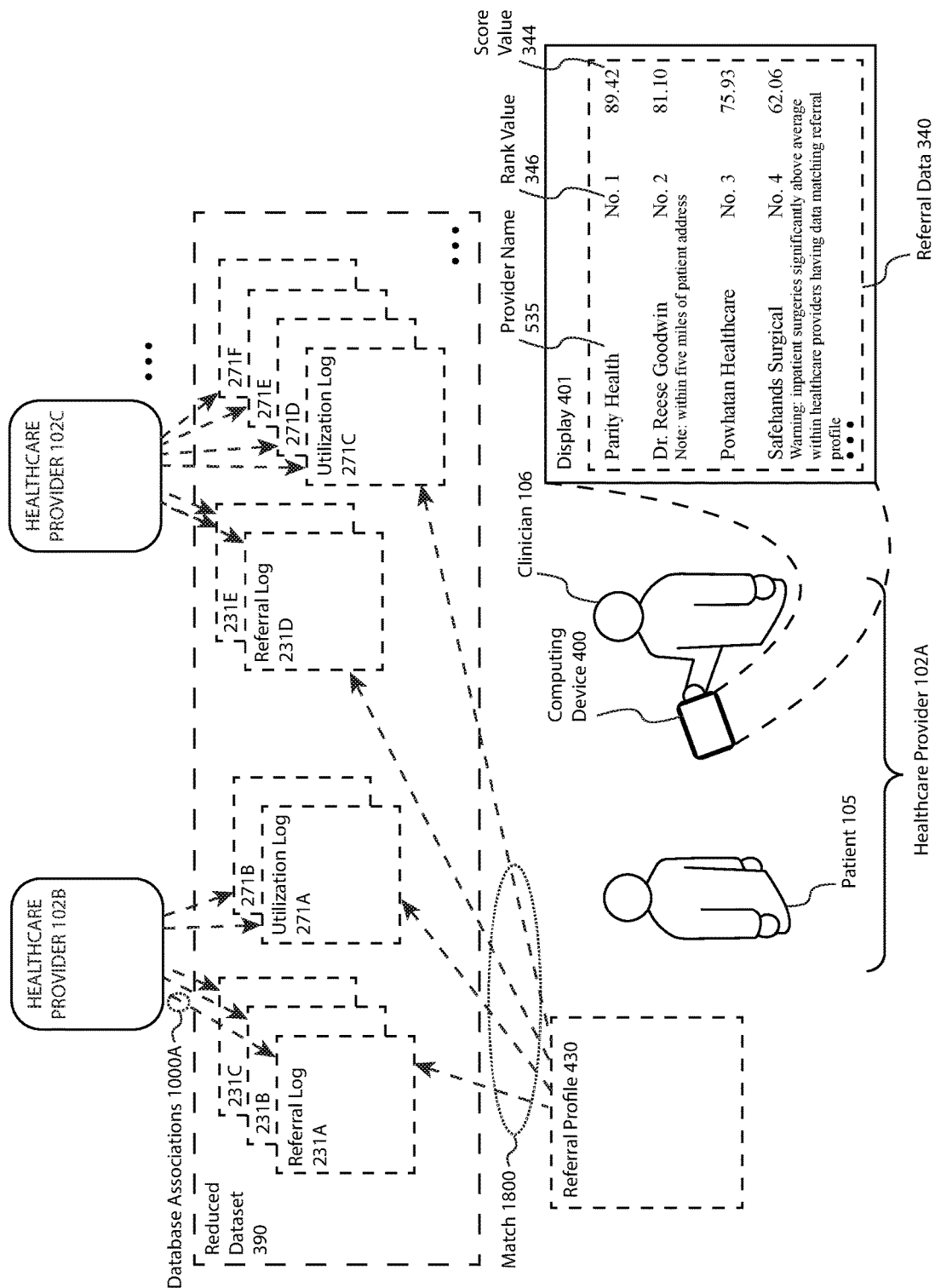
FIG. 18 illustrates an example of generation of a referral data based on the patient profile matched to logs of the reduced dataset, according to one or more embodiments.

FIG. 18 illustrates an example of generation of a referral data based on a patient profile matched to logs of a reduced dataset, according to one or more embodiments. As previously shown and described, a patient 105 may engage in a native encounter with the clinician 106, who may be the healthcare provider 102A. The clinician 106 may wish to refer the patient 105 to a different healthcare provider to receive a service which the clinician 105 is unable to provide.

The referral profile 430 for the patient 105 is generated on the computing device 400 and/or one or more server computers (e.g., the referral server 300), and may be synthesized with data including both manual input data from the patient 105 or clinician 106 and/or automatically retrieved data of the patient 105 (e.g., from the patient profile 511). After submission to the referral server 300, the referral server 300 may generate the reduced dataset 390 according to one or more processes shown and described herein. Although five referral logs 231A through referral log 231E and six utilization logs 271A thorough utilization log 271F are shown, the reduced dataset 390 may include many more instances of the referral log 231 and/or instances of the utilization log 271.

The healthcare provider 102B in the present example is "Parity Health", and may be represented (e.g., identified with a provider group identifier 534) in three instances of the utilization log 271 (the utilization log 271A and the utilization log 271B) and as the referral provider in two instances of the referral log 231 (the referral log 231A through the referral log 231C). The relation may occur through a database association (e.g., a database association 1000A) between the provider profile 531 and each of the logs. The referral profile 430 is shown associated through a determined match (e.g., determined by the profile matching engine 308), shown in FIG. 18 as the match 1800.

Similarly, the healthcare provider 102C may be the practice of Dr. Reese Goodwin, and may be represented with a total of six combined utilization logs 271 (the utilization log 271C through the utilization log 271F) and referral logs 231 (the referral log 231C and the referral log 231D). For clarity, the utilization logs 271 and the referral logs 231 associated with Powhatan Healthcare (e.g., a healthcare provider 102D), and Safehands Surgical (e.g., a healthcare provider 102E) are not shown in the embodiment of FIG. 18.

Following application of the utilization ruleset 316 and/or the referral ruleset 318, as described herein, each of the healthcare providers 102 are scored and/or ranked. The referral data 340 is generated as an output (e.g., by computer readable instructions of the referral server 300). Illustrated in what may be a simple example for clarity, the referral data 340 may include a provider name 535, a rank value 346, and a score value 344. Parity Health scores the highest, at 89.42. and is ranked highest by simple ordering of the score in the present example. Additional information, warnings, or analysis may also be presented. For example, the offices of Dr. Reese Goodwin may be noted to be within a geospatial radius of the healthcare provider 102A and/or an addresses associated with the patient 105. In another example, a reason for Safehand Surgical's lower score may be a relatively poor POS utilization rate 332, even where the Inbound re-referral rate 334 may be high ("Warning: inpatient surgeries significantly above average within healthcare providers having data matching referral profile"). The reason may be part of the access evaluation data 330, processed to be made into an easily readable form from raw data.

Another example embodiment will now be provided in which a health network operates one or more components of the referral evaluation network 100. The health network in this example is an ACO referred to in this example as "Progressive Network" having within the network a healthcare provider 102 referred to as "Longevity Health".

A patient 105 (Abe) may engage in a native encounter with Longevity Health, and specifically a native encounter with an instance of the clinician 106 named Beth. Beth is a primary care physician performing services within a group practice of physicians at Longevity Health focusing exclusively in primary care and internal medicine. Beth works in an office downtown two days per week; the rest of the week, Beth works in the suburbs.

Beth enters the exam room and greets Abe, a 55-year-old man. Beth logs in to a point of care application (e.g., the POC application 404) running on Beth's iPad (e.g., the computing device 400). Beth retrieves health information of Abe's electronic medical record (e.g., from the EMR database 520), including demographic data 515 about Abe—such as age and weight, Abe's health coverage (e.g., the coverage type 516), and Abe's current diagnoses, which may include one or more diagnosis codes 524. Beth briefly reviews the electronic medical record and notices that Abe has lost a significant amount of weight since his last appointment. After her review, Beth asks Abe why Abe came today. Abe explains that he has had trouble with bowel movements recently. Abe reports that he is chronically constipated, and that his bowel movements are painful. Abe also reports that he has noticed blood in his stool. Abe otherwise says he feels healthy. Beth enters this information into the electronic medical record (e.g., to be stored in the EMR database 520).

Based on these reported symptoms, Abe's age, and Abe's recent weight loss, Beth fears Abe may have colon cancer. Beth decides that Abe should undergo a colonoscopy to diagnose the condition or disease that may be causing Abe's symptoms. Beth is not a gastroenterologist and knows she should not perform the colonoscopy herself or otherwise attempt to diagnose the condition. Beth therefore wishes to find a referral provider, a gastroenterologist, to whom Beth will refer Abe for the colonoscopy.

While still in the exam room with Abe, Beth uses the user interface of her iPad to initiate a referral, activating a referral request routine 410 running as part of a software application. Beth enters information necessary about the referral (such as the code for "colonoscopy" in the type of service range), which, when combined with other information pulled from Abe's EMR 521, (such as the patient data 514 extracted from the electronic medical record database 520, and optionally the geolocation of Beth's downtown office), will generate a referral profile 430. To complete the referral profile 430, Beth may also indicate that the preferred place of service is a physician office, since Abe is otherwise generally healthy and does not need to undergo the colonoscopy in a setting (such as a hospital operating room) with resources necessary to serve a higher-risk patient. The selection of a preferred place of service may define the place of service range 450 of the referral profile 430. For example, the referral profile may include a type of service range 452 that includes "colonoscopy", a patient data range 456 that may include Abe's gender and an age group (e.g., 55 to 60 years of age), a coverage type (e.g., HMO, and/or a specific plan such as Blue Cross/Blue Shield®), and a diagnosis code 524. It may be determined a diagnosis code 524 is relevant or irrelevant to referred service. For example, a lookup table may include a list of conditions known to create a high risk of infection, cardiac arrest, or other conditions or complications. However, in the present example Abe does not have any such diagnoses, and so the diagnosis code 524 field may be unspecified. The referral profile 430 is submitted by Beth, and travels over the internet to a server computer (e.g., referral server 300).

A profile matching engine 308 determines utilization logs 271 and/or referral logs 231 that match the referral profile 430. For example, a utilization log 271 may be a match where a healthcare provider 102 provided a colonoscopy to a different patient 105 ("Calvin"), where Calvin was male, within the age of 55 to 60 at the time of treatment, and had the same or a similar coverage type at the time of treatment (and/or in which the healthcare provider 102 is known to currently accept the same or a similar coverage type). A similar matching may occur for referral logs 231.

A dataset reduction subroutine 310 generate a reduced dataset 390, as shown and described in one or more of the present embodiments. In this example, the reduced dataset 390 includes both a number of utilization logs 271 and a number of referral logs 231.

The referral evaluation data 330 generated as an output includes utilization logs 271 and/or referral logs 231 having the following healthcare providers 102 represented in the reduced dataset 390: (1) Metropolitan Cancer Center (a downtown hospital with a gastroenterology department); (2) Suburban Gastroenterology (a group of gastroenterologists working in the suburbs); (3) Cameron, M. D (a gastroenterologist working downtown as a solo practitioner); (4) Daniel, M. D. (a gastroenterologist working downtown in a group practice with other gastroenterologists); and (5) Eastern Gastroenterology Center (a freestanding gastroenterology clinic that performs colonoscopies in an office setting).

The referral rate routine 314 applies the referral ruleset 318 to the reduced dataset 390, in the present example to both score and then rank by score the referral providers that are likely available to receive the referral of Abe's colonoscopy.

Eastern Gastroenterology Center is excluded because Eastern Gastroenterology Center does not accept Abe's health insurance. Metropolitan Cancer Center is excluded because the utilization records 271 of service provided by the Metropolitan Cancer Center indicate that the place of service range 450 is generally "hospital" for colonoscopies (e.g., above a certain threshold, such as 50%). That is, a predominate usage of "hospital" as a place of service does not match the referral profile 430 for Abe's colonoscopy, or may otherwise be specified by the utilization ruleset 316 as disqualifying. For example, Progressive Network may further disqualify or lower any score of Metropolitan Cancer Center because it also performs other diagnostic procedures (e.g., unrelated to colonoscopies) in a hospital setting at a rate above an average rate of healthcare providers within Progressive Network. The usage of a hospital in the utilization record 271 may be specified by CMS POS code 21 and/or by a natural language tagging.

The referral logs 231 and utilization records 271 indicate that Suburban Gastroenterology, Cameron, and Daniel all accept Abe's insurance and all generally have predominate place of service for colonoscopies of "physician office", as may be specified by HMS POS code 11 or by a natural language tagging.

In the present example, geolocation may also be a part of referral profile 430, rather than a subsequent filter applied to results. Suburban Gastroenterology may therefore be removed because the geolocation of Suburban Gastroenterology is outside the geographic area to which Beth would refer a patient 105 (such as Abe) to be seen (e.g., outside the zip code, outside city, a greater distance than 40 miles, etc.).

The referral server 300 in the present example then scores Cameron and Daniel based on additional access to care, using the referral ruleset to evaluate re-referral data and service-on-referral data stored in referral logs 231 for both referral providers. Daniel receives a low score because Longevity Health and/or other referring providers have several referral logs 231 without matching utilization logs 271 to Daniel. Moreover, the referral logs 231 indicate that, for instances of patients 105 referred for gastroenterology procedures to Daniel, many of those patients 105 have been the subject of a re-referral for the same gastroenterology procedure (which may indicate that Daniel does not promptly perform referred gastroenterology procedures, including for referrals by Beth and Longevity Health). In contrast, Cameron may receive a relatively high score because utilization logs 271 and associated referral logs 231 indicate that Cameron has a low rate of re-referral, and because the utilization logs 271 and/or utilization records show that colonoscopies referred to Cameron are generated promptly after receipt.

A ranked list of the qualifying referral providers, in this case Daniel and Cameron, are then transmitted over the network 101 to the computing device 400 (e.g., as part of the referral data 340), which is then displayed to Beth in the user interface 402 of the point-of-care application 404, along with the score for each referral provider (e.g., 3.6 out of 5 for Daniel, 4.8 out of 5 for Cameron).

From the perspective of Beth, the above referral profile submission, log matching, and referral provider scoring, ranking, and presentation may occur almost instantaneously with on-demand processing. Beth then selects Cameron as the referral for Abe's colonoscopy. The referral information is transmitted to Cameron (e.g., Abe's name and relevant details), and a referral log (e.g., the referral log 231) may also be generated to document the referral.

In the present example, Beth efficiently referred Abe in a short period of time and with a data backing her decision. Abe benefits by having a maximized probability of success based on existing data and his individual needs which may be incorporated into the referral profile 430. A maximized positive outcome will bring goodwill and patient satisfaction to Longevity Health and Progressive Network, while also lowering the risk of malpractice or bad patient outcome due to an unsuccessful or inefficient handoff between one healthcare provider and another. In addition, Progressive Network may gain visibility into the referral process and be able to enforce its policies and create incentives through the referral evaluation network 100 that improves efficiencies within the network.

Although the present embodiments have been described with reference to specific example embodiments, it will be evident that various modifications and changes may be made to these embodiments without departing from the broader spirit and scope of the various embodiments. For example, the various devices, engines, agent, routines, and modules described herein may be enabled and operated using hardware circuitry (e.g., CMOS based logic circuitry), firmware, software, or any combination of hardware, firmware, and software (e.g., embodied in a non-transitory machine-readable medium). For example, the various electrical structure and methods may be embodied using transistors, logic gates, and electrical circuits (e.g., application specific integrated circuitry (ASIC) and/or Digital Signal Processor (DSP) circuitry).

In addition, it will be appreciated that the various operations, processes, and methods disclosed herein may be embodied in a non-transitory machine-readable medium and/or a machine-accessible medium compatible with a data processing system (e.g., the log server 200, the referral server 300, the computing device 400, the record server 500). Accordingly, the specification and drawings are to be regarded in an illustrative rather than a restrictive sense.

The structures in the figures such as the engines, routines, and modules may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the preceding disclosure.

Embodiments of the invention are discussed above with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures.

From reading the present disclosure, other variations and modifications will be apparent to persons skilled in the art. Such variations and modifications may involve equivalent and other features which are already known in the art, and which may be used instead of or in addition to features already described herein.

Although claims have been formulated in this application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any claim and whether or not it mitigates any or all of the same technical problems.

Features which are described in the context of separate embodiments may also be provided in combination in a single embodiment. Conversely, various features which are, for brevity, described in the context of a single embodiment, may also be provided separately or in any suitable subcombination. The applicants hereby give notice that new claims may be formulated to such features and/or combinations of such features during the prosecution of the present application or of any further application derived therefrom.

References to "one embodiment," "an embodiment," "example embodiment," "various embodiments," "one or more embodiments," etc., may indicate that the embodiment (s) of the invention so described may include a particular feature, structure, or characteristic, but not every possible embodiment of the invention necessarily includes the particular feature, structure, or characteristic. Further, repeated use of the phrase "in one embodiment," or "in an exemplary embodiment," "an embodiment," do not necessarily refer to the same embodiment, although they may. Moreover, any use of phrases like "embodiments" in connection with "the invention" are never meant to characterize that all embodiments of the invention must include the particular feature, structure, or characteristic, and should instead be understood to mean "at least one or more embodiments of the invention" includes the stated particular feature, structure, or characteristic.

The enumerated listing of items does not imply that any or all of the items are mutually exclusive, unless expressly specified otherwise.

It is understood that the use of a specific component, device and/or parameter names are for example only and not meant to imply any limitations on the invention. The invention may thus be implemented with different nomenclature and/or terminology utilized to describe the mechanisms, units, structures, components, devices, parameters and/or elements herein, without limitation. Each term utilized herein is to be given its broadest interpretation given the context in which that term is utilized.

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

A "computer" may refer to one or more apparatus and/or one or more systems that are capable of accepting a structured input, processing the structured input according to prescribed rules, and producing results of the processing as output. Examples of a computer may include: a computer; a stationary and/or portable computer; a computer having a single processor, multiple processors, or multi-core processors, which may operate in parallel and/or not in parallel; a general purpose computer; a supercomputer; a mainframe; a super mini-computer; a mini-computer; a workstation; a micro-computer; a server; a client; an interactive television; a web appliance; a telecommunications device with internet access; a hybrid combination of a computer and an interactive television; a portable computer; a tablet personal computer (PC); a personal digital assistant (PDA); a portable telephone; a smartphone, application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, a system on a chip, or a chip set; a data acquisition device; an optical computer; a quantum computer; a biological computer; and generally, an apparatus that may accept data, process data according to one or more stored software programs, generate results, and typically include input, output, storage, arithmetic, logic, and control units.

Those of skill in the art will appreciate that where appropriate, one or more embodiments of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Where appropriate, embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

The example embodiments described herein can be implemented in an operating environment comprising computer-executable instructions (e.g., software) installed on a computer, in hardware, or in a combination of software and hardware. The computer-executable instructions can be written in a computer programming language or can be embodied in firmware logic. If written in a programming language conforming to a recognized standard, such instructions can be executed on a variety of hardware platforms and for interfaces to a variety of operating systems. Although not limited thereto, computer software program code for carrying out operations for aspects of the present invention can be written in any combination of one or more suitable programming languages, including an object oriented programming languages and/or conventional procedural programming languages, and/or programming languages such as, for example, Hypertext Markup Language (HTML), Dynamic HTML, Extensible Markup Language (XML), Extensible Stylesheet Language (XSL), Document Style Semantics and Specification Language (DSSSL), Cascading Style Sheets (CSS), Synchronized Multimedia Integration Language (SMIL), Wireless Markup Language (WML), Java™, Jini™, C, C++, Smalltalk, Perl, UNIX Shell, Visual Basic or Visual Basic Script, Virtual Reality Markup Language (VRML), ColdFusion™ or other compilers, assemblers, interpreters or other computer languages or platforms.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

A network is a collection of links and nodes (e.g., multiple computers and/or other devices connected together) arranged so that information may be passed from one part of the network to another over multiple links and through various nodes. Examples of networks include the Internet, the public switched telephone network, the global Telex network, computer networks (e.g., an intranet, an extranet, a local-area network, or a wide-area network), wired networks, and wireless networks.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The flowchart and block diagrams in the figures illustrate the architecture, functionality, and operation of possible implementations of systems, methods and computer program products according to various embodiments. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

Further, although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

It will be readily apparent that the various methods and algorithms described herein may be implemented by, e.g., appropriately programmed general purpose computers and computing devices. Typically a processor (e.g., a microprocessor) will receive instructions from a memory or like device, and execute those instructions, thereby performing a process defined by those instructions. Further, programs that implement such methods and algorithms may be stored and transmitted using a variety of known media.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The functionality and/or the features of a device may be alternatively embodied by one or more other devices which are not explicitly described as having such functionality/features. Thus, other embodiments of the present invention need not include the device itself.

The term "computer-readable medium" as used herein refers to any medium that participates in providing data (e.g., instructions) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, removable media, flash memory, a "memory stick", any other memory chip or cartridge, a carrier wave as described hereinafter, or any other medium from which a computer can read.

Where databases are described, it will be understood by one of ordinary skill in the art that (i) alternative database structures to those described may be readily employed, (ii) other memory structures besides databases may be readily employed. Any schematic illustrations and accompanying descriptions of any sample databases presented herein are exemplary arrangements for stored representations of information. Any number of other arrangements may be employed besides those suggested by the tables shown. Similarly, any illustrated entries of the databases represent exemplary information only; those skilled in the art will understand that the number and content of the entries can be different from those illustrated herein. Further, despite any depiction of the databases as tables, an object-based model could be used to store and manipulate the data types of the present invention and likewise, object methods or behaviors can be used to implement the processes of the present invention.

Embodiments of the invention may also be implemented in one or a combination of hardware, firmware, and software. They may be implemented as instructions stored on a machine-readable medium, which may be read and executed by a computing platform to perform the operations described herein.

More specifically, as will be appreciated by one skilled in the art, aspects of the present invention may be embodied as a system, method or computer program product. Accordingly, aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Unless specifically stated otherwise, and as may be apparent from the following description and claims, it should be appreciated that throughout the specification descriptions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

The term "processor" may refer to any device or portion of a device that processes electronic data from registers and/or memory to transform that electronic data into other electronic data that may be stored in registers and/or memory. A "computing platform" may comprise one or more processors.

Those skilled in the art will readily recognize, in light of and in accordance with the teachings of the present invention, that any of the foregoing steps and/or system modules may be suitably replaced, reordered, removed and additional steps and/or system modules may be inserted depending upon the needs of the particular application, and that the systems of the foregoing embodiments may be implemented using any of a wide variety of suitable processes and system modules, and is not limited to any particular computer hardware, software, middleware, firmware, microcode and the like. For any method steps described in the present application that can be carried out on a computing machine, a typical computer system can, when appropriately configured or designed, serve as a computer system in which those aspects of the invention may be embodied.

It will be further apparent to those skilled in the art that at least a portion of the novel method steps and/or system components of the present invention may be practiced and/or located in location(s) possibly outside the jurisdiction of the United States of America (USA), whereby it will be accordingly readily recognized that at least a subset of the novel method steps and/or system components in the foregoing embodiments must be practiced within the jurisdiction of the USA for the benefit of an entity therein or to achieve an object of the present invention.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Having fully described at least one embodiment of the present invention, other equivalent or alternative methods of implementing the certification network 100 according to the present invention will be apparent to those skilled in the art. Various aspects of the invention have been described above by way of illustration, and the specific embodiments disclosed are not intended to limit the invention to the particular forms disclosed. The particular implementation of the loyalty rewards programs may vary depending upon the particular context or application. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims. The following claims are hereby incorporated into the detailed description, with each claim standing on its own as a separate embodiment.

We claim:

1. A method for structuring electronic data logs for efficient determination of a healthcare referral provider from a point-of-care application, the method comprising:

determining generation of a healthcare utilization record comprising a patient UID of a first patient and a provider UID of a first healthcare provider;

determining a place of service value that describes a type of facility associated with the healthcare utilization record;

determining a type of service associated with the healthcare utilization record;

generating a first utilization log comprising the provider UID of the first healthcare provider, the place of service value, a type of service value, and a utilization time associated with at least one of providing a healthcare service to the first patient and generation of the healthcare utilization record;

storing a utilization log in an electronic database storing a log data structure comprising: (i) a set of data each modeling healthcare providers associated by one or more referral logs, and (ii) a set of utilization logs each associated with a data from the set of data each modeling healthcare providers;

initiating a referral request on a user interface of a clinical documentation workflow of the point-of-care application running on a computing device of a second healthcare provider to refer a second patient of the second healthcare provider to a referral provider;

generating a referral profile for the second patient, the referral profile comprising a place of service range, a type of service range, and a time range, extracting the set of utilization logs from a utilization database, wherein the set of utilization logs comprises the first utilization log comprising the place of service value, and wherein the set of utilization logs each comprise at least one of the place of service value and a different instance of the place of service value;

comparing the referral profile to the set of utilization logs;

generating a reduced dataset comprising a subset of utilization logs extracted from the set of utilization logs matching the referral profile, wherein a number of healthcare providers associated with the reduced dataset is compared to a minimum threshold of healthcare providers to determine a sufficient number of healthcare providers within the reduced dataset;

calculating, using the subset of utilization logs in the reduced dataset, a POS utilization rate of the first healthcare provider for each instance of the place of service value within the place of service range, wherein the POS utilization rate is a set of percentage values, each percentage value a number of utilization logs in the reduced dataset comprising an instance of the place of service value within the place of service range relative to a total number of utilization logs in the reduced dataset;

applying a utilization ruleset to at least one of score, rank, and qualify the first healthcare provider based on criteria comprising the POS utilization rate;

adding the provider UID of the first healthcare provider to a referral data; and transmitting the referral data over a network from a server to the computing device of the second healthcare provider running the point-of-care application, where the referral data is integrated within the user interface of the clinical documentation workflow of the point-of-care application.

2. The method of claim 1, further comprising:

querying a patient profile of the first patient with the patient UID of the first patient; and extracting from the patient profile of the first patient a patient data comprising at least one of a demographic data of the first patient, a coverage type of the first patient, and a diagnosis code of the first patient, wherein the first utilization log further comprising the patient data, wherein the referral profile further comprising a patient data range, and wherein the patient data range comprising at least one of a demographic data of the second patient, a coverage type of the second patient, and a diagnosis code of the second patient.

3. The method of claim 2, further comprising:

calculating, using a different set of utilization logs of two or more healthcare providers within the utilization database, a POS utilization rate of the two or more healthcare providers for each instance of the place of service value within the place of service range, wherein at least one of the scoring, the ranking, and the qualifying of the first healthcare provider is based on criteria comprising the POS utilization rate of the first healthcare provider relative to a statistical average of the POS utilization rate of the two or more healthcare providers calculated from the utilization database.

4. The method of claim 3, further comprising:

receiving a selection of the second healthcare provider from a clinician through the point-of-care application; and automatically scheduling an appointment for the second patient with the first healthcare provider.

5. The method of claim 4, further comprising:

extracting from the patient profile of the second patient a location data associated with the second patient; and determining the second healthcare provider is within a predetermined distance based on the location data.

6. The method of claim 5, wherein the utilization ruleset determines that the instance of the place of service value is a preferred instance of the place of service value based on criteria comprising the type of service.

7. The method of claim 6, wherein the type of service value is at least one of a service category and a procedure code value, wherein the procedure code value is a CPT code value, wherein the place of service value is stored in computer memory as a POS code value, and wherein at least one of the place of service range, the type of service range, the patient data range, and the time range of the referral profile is selected by the clinician through the point-of-care application.

8. A method for constructing and utilizing a log data structure for maximizing healthcare referral outcomes, comprising:

detecting a first healthcare referral of a first patient, the first healthcare referral from a first healthcare provider to a second healthcare provider;

generating a first referral log comprising a provider UID of the first healthcare provider, a provider UID of the second healthcare provider, a referral time of the first healthcare referral, and a type of service;

storing the first referral log in an electronic database storing the log data structure comprising: (i) a set of data each modeling healthcare providers associated by a set of referral logs, (ii) a set of utilization logs each linked to a data modeling at least one healthcare provider through a database association linking a utilization log to a data modeling a healthcare provider, (iii) a database association linking two or more referral logs within the set of referral logs, and (iv) a database association linking at least one of the set of utilization logs with at least one of the two or more referral logs, wherein the first referral log is stored as a database association linking a data modeling the first healthcare provider to a data modeling the second healthcare provider;

detecting a second healthcare referral of the first patient, the second healthcare referral from the second healthcare provider to a third healthcare provider;

generating a second referral log comprising the provider UID of the second healthcare provider, a provider UID of the third healthcare provider, a referral time of the second healthcare referral, and the type of service;

storing the second referral log as a database association linking the data modeling the second healthcare provider to a data modeling the third healthcare provider within the log data structure;

determining a referral association between the first healthcare referral and the second healthcare referral;

storing a first database association in the log data structure linking the second referral log and the first referral log;

initiating a referral request to refer a second patient to a referral healthcare provider;

generating a referral profile for the second patient, the referral profile comprising a type of service range and optionally a place of service range;

comparing the referral profile to a referral dataset comprising the set of referral logs that are associated with the provider UID of the second healthcare provider, wherein the set of referral logs that are associated with the provider UID of the second healthcare provider comprise a data storing at least one of a database association drawn into the data modeling the second healthcare provider and a database association drawn out of the data modeling the second healthcare provider, generating a reduced dataset comprising a subset of the set of referral logs extracted from the referral dataset matching the referral profile, wherein at least one of the first referral log and the second referral log matches the referral profile, and wherein a number of healthcare providers associated with the reduced dataset is compared to a minimum threshold of healthcare providers to determine a sufficient number of healthcare providers within the reduced dataset;
referencing a first time period value;
determining, using the subset of the set of referral logs in the reduced dataset, an inbound re-referral rate of the second healthcare provider within the first time period value,
   wherein the inbound re-referral rate is calculated as a proportion of (i) the subset of the set of referral logs that each store a database association drawn into the data modeling the second healthcare provider and that comprise a database association linking one or more of the subset of the set of referral logs that store a database association drawn out of the data modeling the second healthcare provider, where a timestamp of each referral log storing the database association drawn into the data modeling the second healthcare provider and a timestamp of each referral log storing the database association drawn out of the data modeling the second healthcare provider are within the first time period value, relative to (ii) other instances within the subset of the set of referral logs that each store the database association drawn into the data modeling the second healthcare provider;
applying a referral ruleset to at least one of score, rank, and qualify the second healthcare provider based on criteria comprising the inbound re-referral rate of the second healthcare provider; and
adding the provider UID of the second healthcare provider to a referral data.

9. The method of claim 8, further comprising:
transmitting the referral data over a network from a server to a computing device of the second patient;
receiving a selection of the second healthcare provider from the second patient on the computing device of the second patient; and
automatically scheduling an appointment for the second patient with the first healthcare provider.

10. The method of claim 9, further comprising:
querying a patient profile of the first patient with a patient UID of the first patient; and
extracting from the patient profile of the first patient a patient data comprising at least one of a demographic data of the first patient, a coverage type of the first patient, and a diagnosis code of the first patient,
   wherein at least one of the first referral log and the second referral log further comprising the patient data, and
   wherein the referral profile further comprising a patient data range comprising at least one of a demographic data of the second patient, a coverage type of the second patient, and a diagnosis code of the second patient.

11. The method of claim 8, further comprising:
determining generation of a healthcare utilization record comprising a patient UID of the first patient and the provider UID of the second healthcare provider;
generating a utilization log comprising the provider UID of the first healthcare provider, the type of service, and optionally comprising a place of service value that describes a type of facility and a utilization time associated with at least one of utilization of a healthcare service and generation of the utilization log;
determining the utilization log of the first patient corresponds to the first referral log;
storing a second database association linking the utilization log and at least one of the second referral log and the first referral log; and
transmitting the referral data over a network from a server to a computing device of the second healthcare provider running a point-of-care application, where the referral data is integrated within a user interface of a clinical documentation workflow of the point-of-care application.

12. The method of claim 11, further comprising:
referencing a second time period value;
determining the utilization time is within the second time period value; and
reducing the inbound re-referral rate of the second healthcare provider.

13. The method of claim 11, further comprising:
calculating, using the subset of the set of referral logs and a subset of utilization logs in the reduced dataset, a service-on-referral rate of the second healthcare provider,
   wherein the referral ruleset applied to at least one of score, rank, and qualify the second healthcare provider is based on criteria further comprising the service-on-referral rate of the second healthcare provider.

14. The method of claim 11, further comprising:
calculating a first instance of the inbound re-referral rate of the second healthcare provider,
   wherein the second healthcare provider is an individual provider;
calculating a second instance of the inbound re-referral rate of a provider group to which the individual provider is associated; and
generating a weighted instance of the inbound re-referral rate of the second healthcare provider based on the first instance of the inbound re-referral rate and the second instance of the inbound re-referral rate.

15. The method of claim 14,
wherein the first time period value is dependent on the type of service,
wherein the type of service is a procedure code value,
wherein the procedure code value is a CPT code value,
wherein the place of service value is stored in computer memory as a POS code value, and
wherein at least one of the place of service range, the type of service range, and a patient data range is selected by a clinician through the point-of-care application.

16. A system, comprising:
a log server comprising:
   a processor of the log server,
   a memory of the log server,
   a set of healthcare utilization logs, each comprising a provider UID of a healthcare provider, one or more instances of a type of service value, and one or more instances of a place of service value describing a type of facility,
   a set of referral logs each comprising a provider UID of a referral provider, a provider UID of a referring provider, the one or more instances of the type of service value, and the one or more instances of the place of service value,
   a first set of database associations associating one or more of the set of utilization logs with one or more of the set of referral logs,
   a second set of database associations associating one or more of the set of referral logs with one or more of a different set of referral logs from the referring provider to a different healthcare provider as a different referral provider, an electronic database storing a log data structure comprising: (i) a set of data each modeling a healthcare provider each connected by database associations defined by the set of referral logs, (ii) the set of utilization logs each associated through a database association linking a utilization log of the set of utilization logs to a data modeling the healthcare provider, (iii) a database association linking two or more referral logs within the set of referral logs, and (iv) a database association linking at least one of the set of utilization logs with at least one of the two or more referral logs;

a referral server, comprising:
  a processor of the referral server;
  a referral request agent comprising computer readable instructions that when executed on the processor of the of the referral server:
    receives a referral request to refer a patient for healthcare services; and
    at least one of generates and receives a referral profile;
  a profile matching engine comprising computer readable instructions that when executed on the processor of the of the referral server:
    compares the referral profile to the set of referral logs and the set of utilization logs; and
    determines matching instances of the set of utilization logs and the set of referral logs to the referral profile;
  a dataset reduction subroutine comprising computer readable instructions that when executed on the processor of the of the referral server:
    generates a reduced dataset comprising a subset of the set of utilization logs, and a subset of the set of referral logs matching the referral profile,
      wherein a number of healthcare providers associated with the reduced dataset is compared to a minimum threshold of healthcare providers to determine a sufficient number of healthcare providers within the reduced dataset;
  a utilization rate routine comprising computer readable instructions that when executed on the processor of the of the referral server:
    calculates, using the subset of the set of utilization logs in the reduced dataset, a POS utilization rate of a referral healthcare provider for each instance of the place of service value,
      wherein the POS utilization rate is a set of percentage values, each percentage value a number of utilization logs in the reduced dataset comprising an instance of the place of service value within a place of service range relative to a total number of utilization logs in the reduced dataset;
  a referral rate routine comprising computer readable instructions that when executed on the processor of the of the referral server:
    calculates, using the subset of the set of referral logs in the reduced dataset, an inbound re-referral rate of the referral healthcare provider;
      wherein the inbound re-referral rate is calculated as a proportion of (i) the subset of the set of referral logs that each store a database association drawn into the data modeling the referral healthcare provider and that comprise a database association linked to one or more of the subset of the set of referral logs that store a database association drawn out of the data modeling the referral healthcare provider, where a timestamp of each referral log storing the database association drawn into the data modeling the referral healthcare provider and a timestamp of each referral log storing the database association drawn out of the data modeling the referral healthcare provider are within a first time period value, relative to (ii) other instances within the subset of the set of referral logs that each store database associations drawn into the data modeling the referral healthcare provider;
  a hybrid ruleset specifying criteria for to at least one of score, rank, and qualify the healthcare provider based on criteria comprising the POS utilization rate and the inbound re-referral rate,
  a referral generation subroutine comprising computer readable instructions that when executed on the processor of the of the referral server:
    generates a referral data comprising the provider UID of the referral provider, a name of the referral provider, and optionally a referral evaluation data comprising at least one of a score, a rank, and a qualification resulting from application of the hybrid ruleset on the reduced dataset, and
a network.

17. The system of claim 16, further comprising:
a record server, comprising:
  a processor of the record server,
  a memory of the record server, and
  a claim database comprising a healthcare utilization record comprising the provider UID of the referral provider, and at least one of the type of service value and the place of service value,
wherein the log server further comprising:
  a referral extraction routine comprising computer readable instructions that when executed on the processor of the log server:
    determines the provider UID the referral provider,
    determines the provider UID of the referring provider,
    determines the type of service value,
    determines the one or more instances of the place of service value; and
  a utilization extraction routine comprising computer readable instructions that when executed on the processor of the log server:
    determines the provider UID of the healthcare provider,
    determines the instance of the place of service value based on a data of the healthcare utilization record, and
    determines the type of service value based on a data of the healthcare utilization record.

18. The system of claim 17, wherein the log server further comprising:
a log storage module comprising computer readable instructions that when executed on the processor of the log server:
  generates a referral log comprising the provider UID of the healthcare provider and the type of service value; and
  generates a first utilization log comprising the provider UID of the healthcare provider, the place of service value, and the type of service value; and a log association system comprising computer readable instructions that when executed on the processor of the log server:
  determines associations between at least one of (i) the first utilization log and the referral log, and (ii) the referral log and a different referral log,
  stores a pointer associating at least one of (i) the first utilization log with the referral log, and (ii) the referral log with the different referral log.

19. The system of claim 18, further comprising:
a computing device comprising:
  a processor of the computing device,
  a memory of the computing device,
  a point-of-care application comprising a referral request routine enabling a clinician to initiate a healthcare referral of the patient within a clinical documentation workflow of the point-of-care application,
  a referral profile generation routine comprising computer readable instructions that when executed on the processor of the computing device
    initiates the referral profile: and
    stores in the referral profile the place of service range and optionally a type of service range, a patient data range, and a time range,
  an integration routine comprising computer readable instructions that when executed on the processor of the computing device:
    receives the referral data from the referral server; and
    displays the referral data in the clinical documentation workflow of the point-of-care application; and
  a referral selection routine comprising computer readable instructions that when executed on the processor of the computing device:
    receives a selection of the healthcare provider from the clinician; and
    returns the provider UID of the healthcare provider over the network.

20. The system of claim 19, wherein
at least one of the set of referral logs and at least one of the set of utilization logs comprising at least one of a demographic data, a coverage type, and a diagnosis code,
the referral profile comprising a patient UID, and
the log server, further comprises:
  a patient query engine comprising computer readable instructions that when executed on the processor of the log server:
    queries a profile of the patient; and
    receives at least one of a demographic data of the patient, a coverage type of the patient, and an instance of the diagnosis code that is related to the patient.

* * * * *